US011883546B2

(12) United States Patent
Ramer et al.

(10) Patent No.: US 11,883,546 B2
(45) Date of Patent: Jan. 30, 2024

(54) LUMINAIRE WITH DISINFECTION LIGHT EXPOSURE AND DOSAGE LIMIT CONTROL PROTOCOL AND SENSOR INTEGRATION

(71) Applicant: ABL IP HOLDING LLC, Conyers, GA (US)

(72) Inventors: David P. Ramer, Reston, VA (US); Jack C. Rains, Jr., Sarasota, FL (US); Yan Rodriguez, Suwanee, GA (US); Ron Carl Schimmelpfenning, Winona, MN (US); Jeannine Fisher Wang, Orinda, CA (US)

(73) Assignee: ABL IP HOLDING LLC, Conyers, GA (US)

( * ) Notice: Subject to any disclaimer, the term of this patent is extended or adjusted under 35 U.S.C. 154(b) by 527 days.

(21) Appl. No.: 17/005,971

(22) Filed: Aug. 28, 2020

(65) Prior Publication Data
US 2022/0062463 A1   Mar. 3, 2022

(51) Int. Cl.
*A61L 2/10* (2006.01)
*H05B 47/16* (2020.01)
*H05B 45/30* (2020.01)

(52) U.S. Cl.
CPC .............. *A61L 2/10* (2013.01); *H05B 45/30* (2020.01); *H05B 47/16* (2020.01)

(58) Field of Classification Search
CPC .......... A61L 2/10; A61L 2/24; A61L 2202/11; A61L 2202/14; A61L 2202/25;
(Continued)

(56) References Cited

U.S. PATENT DOCUMENTS 5,289,358 A   2/1994   Halemeier
5,623,105 A   4/1997   Liston et al.
(Continued)

FOREIGN PATENT DOCUMENTS

CA   2258475 A1   7/1999
EP   1925709 A1   5/2008
(Continued)

OTHER PUBLICATIONS

Healthe by Lighting Science, "Cleanse® Downlight Owner's Manual," © 2020 Healthe Lighting, Cleanse_Downlight_Manual_061820, http://www.globenewswire.com/news-release/2020/06/01/2041460/0/en/Acuity-Brands-Announces-Agreement-with-Ushio-America-Inc.html, printed Sep. 2, 2020, 3 pages.
(Continued)

*Primary Examiner* — Regina M Yoo
(74) *Attorney, Agent, or Firm* — RatnerPrestia

(57) ABSTRACT

A luminaire includes a luminaire control circuit and a disinfection light source to emit a disinfection light in an ultraviolet (UV) band for disinfecting a vicinity of a space of a target pathogen that is exposed to the disinfection light. The UV band is 200 nanometers (nm) to 230 nm wavelength. The luminaire initiates a dose cycle of a vicinity in which the disinfection light source emits the disinfection light continuously or during a plurality of periods of a dose cycle from the disinfection light source by recording a beginning time of the dose cycle. The luminaire controls, via a driver circuit, the disinfection light source over the dose cycle to emit the disinfection light continuously or during the plurality of periods for disinfecting the vicinity to substantially obtain a target pathogen UV radiation level and restrict a total UV radiation threshold exposure level by a UV radiation threshold limit.

17 Claims, 9 Drawing Sheets

(58) Field of Classification Search
CPC ...... H05B 45/30; H05B 47/16; H05B 47/115; H05B 47/175; Y02B 20/40; F24F 8/22; F24F 2221/02
See application file for complete search history.

(56) References Cited

U.S. PATENT DOCUMENTS

| | | | |
|---|---|---|---|
| 5,770,147 | A | 6/1998 | Muller |
| 5,859,952 | A | 1/1999 | Levine et al. |
| 6,403,030 | B1 | 6/2002 | Horton, III |
| 6,586,890 | B2 | 7/2003 | Min et al. |
| 7,270,748 | B1 | 9/2007 | Lieggi |
| 7,296,422 | B2 | 11/2007 | Strohm et al. |
| 7,419,642 | B2 | 9/2008 | Fowler et al. |
| 7,498,009 | B2 | 3/2009 | Leach et al. |
| 7,713,426 | B2 | 5/2010 | Newcombe |
| 7,862,728 | B2 | 1/2011 | Yencho |
| 8,398,264 | B2 | 3/2013 | Anderson et al. |
| 8,420,022 | B2 | 4/2013 | Soler et al. |
| 8,465,172 | B2 | 6/2013 | Marson |
| 8,481,985 | B2 | 7/2013 | Neister |
| 8,506,886 | B2 | 8/2013 | Owen et al. |
| 8,753,575 | B2 | 6/2014 | Neister |
| 8,975,605 | B2 | 3/2015 | Neister |
| 8,980,171 | B2 | 3/2015 | Mazyck et al. |
| 9,039,966 | B2 | 5/2015 | Anderson et al. |
| 9,333,274 | B2 | 5/2016 | Peterson et al. |
| 9,597,420 | B2 | 3/2017 | Maxik et al. |
| 9,700,641 | B2 | 7/2017 | Hawkins et al. |
| 9,700,642 | B2 | 7/2017 | Neister |
| 9,839,706 | B2 | 12/2017 | Anderson et al. |
| 10,207,015 | B2 | 2/2019 | Dayton |
| 10,226,541 | B2 | 3/2019 | Trapani |
| 2005/0169795 | A1 | 8/2005 | Sanchez |
| 2009/0145855 | A1 | 6/2009 | Day et al. |
| 2009/0191100 | A1 | 7/2009 | Deal |
| 2009/0208386 | A1 | 8/2009 | Barsky et al. |
| 2010/0032589 | A1 | 2/2010 | Leben |
| 2010/0222852 | A1 | 9/2010 | Vasily et al. |
| 2010/0237254 | A1 | 9/2010 | Mason et al. |
| 2012/0287245 | A1 | 11/2012 | Holland et al. |
| 2015/0335246 | A1 | 11/2015 | Rains, Jr. et al. |
| 2017/0246331 | A1* | 8/2017 | Lloyd .................... A61Q 17/04 |
| 2018/0255622 | A1* | 9/2018 | Spero .................... H05B 3/008 |
| 2019/0247528 | A1 | 8/2019 | Rodriguez |
| 2020/0073199 | A1 | 3/2020 | Lin et al. |

FOREIGN PATENT DOCUMENTS

| | | |
|---|---|---|
| EP | 3417348 B1 | 10/2020 |
| JP | 1998314280 A | 12/1998 |
| JP | 2005168858 A | 6/2005 |
| RU | 104068 U1 | 5/2011 |
| WO | 2012078476 A2 | 6/2012 |
| WO | 2012122511 A1 | 9/2012 |

OTHER PUBLICATIONS

High Energy Ozone, LLC—UV Sterilization Technology, "Technology For Improving Health," https://heo3.com/ Aug. 8, 2018, 14 pages.

Manuela Buonanno, "Germicidal Efficacy and Mammalian Skin Safety of 222-nm UV Light," HHS Public Access, Author manuscript, Radiat Res. Author manuscript; available in PMC Aug. 10, 2017, 18 pages.

Acuity Brands, "Acuity Brands Announces Agreement with Ushio America, Inc.," Jun. 1, 2020, http://www.globenewswire.com/news-release/2020/06/01/2041460/0/en/Acuity-Brands-Announces-Agreement-with-Ushio-America-Inc.html, printed Sep. 2, 2020, 2 pages.

* cited by examiner

LUMINAIRE WITH DISINFECTION LIGHT EXPOSURE AND DOSAGE LIMIT CONTROL PROTOCOL AND SENSOR INTEGRATION

TECHNICAL FIELD

The present subject matter relates to disinfection lighting devices, luminaires incorporating disinfection light components, and techniques of operating such equipment to provide disinfection light, e.g., ultraviolet (UV) light, to deactivate a pathogen for an antimicrobial application, e.g., for disinfection.

BACKGROUND

Disinfection light, such as ultraviolet (UV) light, is known to deactivate various types of pathogens. In recent years, there have been various proposals to incorporate, in general lighting equipment, light sources specifically configured to deactivate bacteria, viruses, and other pathogens on a surface, such as Methicillin-Resistant Staphylococcus Aureus (MRSA) on work surfaces, sinks, floors etc. of hospitals, nursing homes or the like.

A number of these proposals have suggested use of disinfection light at or around 405 nanometers (nm), that is to say, in the near-ultraviolet end of the visible spectrum. Some examples of such equipment have utilized light in a wavelength range that includes at least a portion in the humanly visible spectrum for the disinfection light, e.g., disinfection light having a maximum peak at a wavelength in a range of 400 nanometers (nm) to 450 nm, which may be perceptible as visible light during disinfection operations. Other types of lighting equipment providing a disinfection illumination function or service, however, may utilize appropriate wavelengths in the range from 180 nm to 380 nm in the ultraviolet portion of the spectrum that is not visible to a human during a disinfection operation. At least some UV wavelengths appear to be more efficacious for disinfection than visible wavelengths. Although some UV wavelengths (e.g. far-UVC in the range of 200 nm to 230 nm), if used properly, may have little or no harmful effect on human occupants, other UV wavelengths suitable for disinfection may be harmful to the people in the area. However, even far-UVC light, if used improperly, can still be harmful to humans.

For many UV applications, such as disinfection, effectiveness requires at least a certain minimum intensity of the applied UV light. For example, to ensure effective disinfection of a surface or air in a room in a hospital or the like, it may be necessary to apply UV of a particular intensity for a specific duration of time. The application of sufficient intensity over a specific duration serves to apply a cumulative amount of UV light energy so as to deactivate or kill pathogens, such as viruses, bacteria, protozoans, fungi, such as mold, or other harmful microorganisms.

As noted above, UV light for disinfection or other functions is not visible to a human. Unlike general illumination with visible light, a person in or entering a space being treated might not realize that a luminaire is outputting UV light. Possible acute and chronic damage to eyes and skin may result from the UV wavelength used in many germicidal lamps. Certain bands of UV light (e.g., UVB) penetration of human tissue can cause sunburn, skin cancer, cataracts, photokeratitis, and other conditions. In addition, although disinfection light lamps in lower end of the visible light range, such as the 405-430 nm wavelength range can be used for disinfection in occupied spaces, the 405-430 nm is not as effective against viruses as UV light and typically require a much longer duration of exposure for disinfection of a surface.

Accordingly, UV light exposure and dosage limit controls are needed to safely control human exposure to UV light emission in a potentially harmful wavelength range while allowing for more rapid disinfection of a target pathogen on a surface or suspended in air. The examples described herein describe safety limits to avoid an unsafe amount of human exposure to excessive UV light radiation.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1:
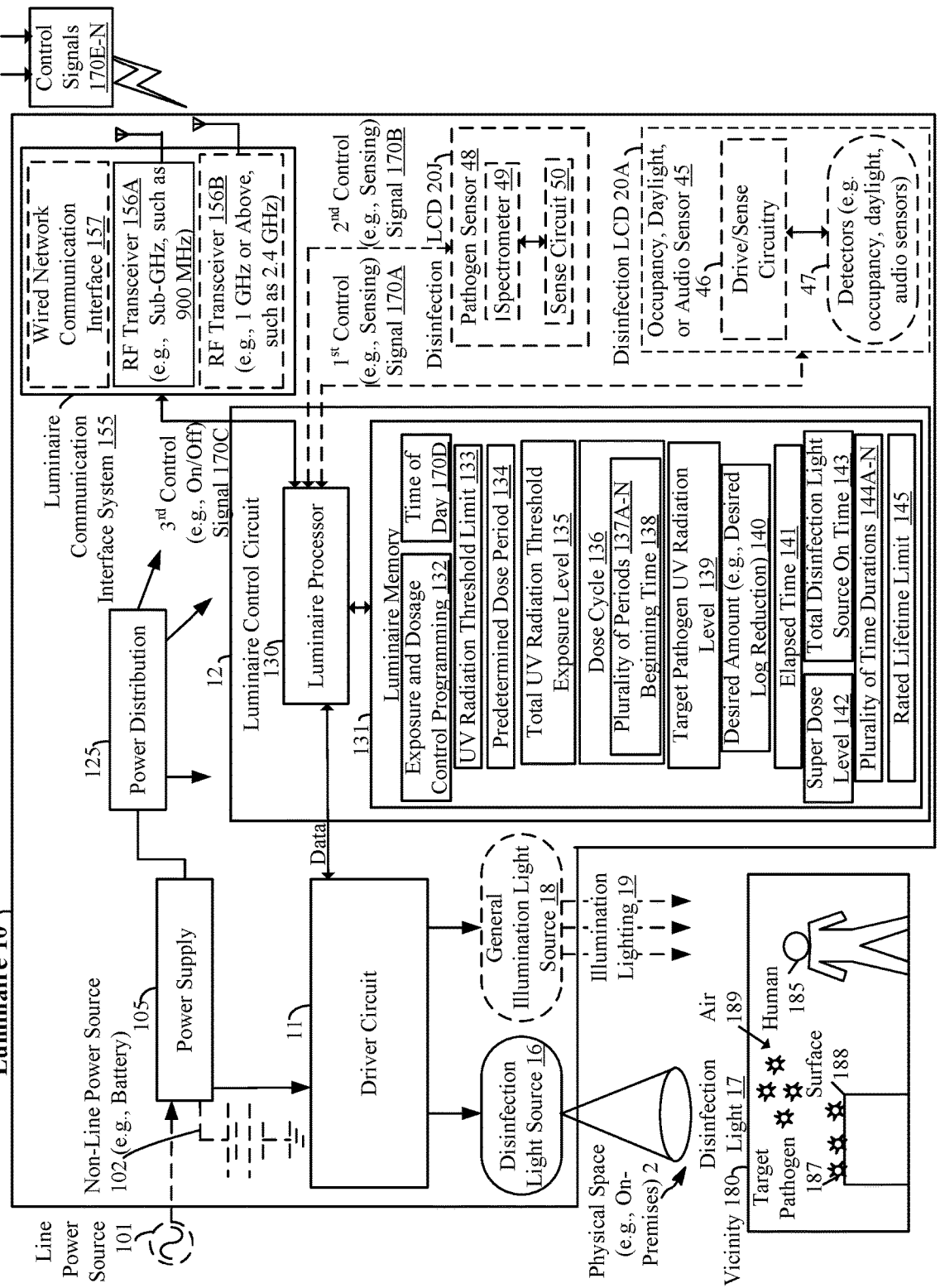
FIG. 1 is a block diagram of a luminaire that implements a disinfection light exposure and dosage limit control protocol.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The various examples disclosed herein relate to an antimicrobial system 1 that includes lighting devices for disinfection and to luminaire(s) 10 incorporating a disinfection light source 16 and an optional general illumination light source 18. The luminaire(s) 10 includes exposure and dosage limit control techniques for such disinfection of a target pathogen 187 on a surface 188 or suspended in air 189. The disinfection light 17 produced has properties (e.g. wavelength, energy and/or time duration) suitable to deactivation of one or more potentially harmful target pathogen(s) 187.

Target pathogen(s) 187, for example, include microorganisms, bacteria, viruses (e.g., coronavirus, norovirus, etc.), protozoa, prions, fungal spores, and other infectious agents. Such a target pathogen 187 is deactivated, for example, if the disinfection light exposure deactivates the pathogen or otherwise damages the target pathogen 187 (e.g. ruptures the cell membrane or breaks DNA or RNA chain in the pathogen) so as to limit or prevent the harmful function of the target pathogen 187.

Although the discussion herein is focused on light fixture type luminaire(s) 10 that have a fixed position in a space, it should be understood that other types of luminaire(s) 10 can be used/sensed in lieu of light fixtures, such as lamps. The term "luminaire" 10 as used herein, is intended to encompass essentially any type of device, e.g., a light fixture or a lamp that processes energy to generate or supply disinfection light 17 from a disinfection light source 16. The luminaire 10 optionally emits artificial illumination lighting 19 from a general illumination light source 18, for example, for general illumination of a physical space 2 intended for use of or occupancy or observation, typically by a living organism that can take advantage of or be affected in some desired manner by the light emitted from the device. The luminaire 10 may provide the optional artificial illumination lighting 19 for use by automated equipment, such as sensors/monitors, robots, etc. that may occupy or observe the illuminated physical space 2, instead of or in addition to light provided for an organism. However, it is also possible that one or more luminaire(s) 10A-N in or on a particular premises have other lighting purposes, such as signage for an entrance or to indicate an exit. In most examples, the luminaire(s) 10A-N disinfect a physical space 2 of a target pathogen 187 and optionally illuminate a physical space 2 of a premises to a level useful for a human 185 in or passing through the space 2, e.g. general illumination lighting 19 of an office, room, or corridor in a building or of an outdoor physical space 2 such as a street, sidewalk, parking lot or performance venue. The actual disinfection light source 16 of the luminaire 10 that emits disinfection light 17 may be any type of light emitting device, several examples of which are included in the discussions below. Each example of the luminaire 10 with integrated disinfection capability described later includes a disinfection light source 16.

The "luminaire" 10 can include other elements such as electronics and/or support structure, to operate and/or install the particular luminaire implementation. Such electronics hardware, for example, may include some or all of the appropriate driver(s) for the disinfection light source 16 and optional general illumination light source 18, any associated control processor or alternative higher level control circuitry, and/or data communication interface(s). As noted, the lighting component(s) are located into an integral unit, such as a light fixture or lamp implementation of the luminaire 10. The electronics for driving and/or controlling the lighting component(s) may be incorporated within the luminaire 10 or located separately and coupled by appropriate means to the light source component(s).

The term "antimicrobial system" 1, "lighting control system," or "lighting system" as used herein, is intended to encompass essentially any type of system that either includes a number of such luminaires 10A-N coupled together for data communication and/or luminaire(s) including or coupled together for data communication with one or more disinfection light control devices 20A-M, such as occupancy, audio, or daylight sensors 45A-C, wall switches 46A-C, control panels (e.g., touch screen devices 47A-C), pathogen sensors 48A-C, mobile device 25, remote controls, central lighting or building control systems, servers, etc.

The disinfection light 17 of a luminaire 10, for example, may have an intensity and/or other characteristic(s) that satisfy an industry acceptable performance standard for disinfection of surface(s) 188 or air 189 in a vicinity 180 of the physical space 2. The term "antimicrobial" means to disinfect by disinfecting or otherwise deactivating, killing, or slowing the spread of the target pathogen 187. The term "disinfect" means to reduce an amount of target pathogen 187 by a desired amount 140, for example, by a desired log reduction. The disinfection performance standard may vary for different uses or applications of the physical space 2, for example, as between residential, medical, hospital, office, manufacturing, warehouse, or retail spaces. Moreover, the disinfection performance standard may vary among multiple vicinities 180A-D of the physical space 2, for example, a physical space 2 may subdivided into different areas requiring varying levels of disinfection requirements, such as a desired amount 140 (e.g., desired log reduction). Any luminaire 10, however, may be controlled in response to commands received with the network technology of the antimicrobial system 1, e.g. to turn the disinfection light source 16 on ON/OFF, to dim the light intensity of the disinfection light 17, to adjust the disinfection light 17 output, etc.

Terms such as "disinfection light" 17 when referring to the disinfection light source 16 or "artificial lighting" or "illumination lighting" 19 when referring to the general illumination light source 18, are intended to encompass essentially any type of lighting in which a luminaire 10 produces light by processing of electrical power to generate the light. A luminaire 10 for disinfection light 17, for example, may take the form of a lamp, light fixture, or other luminaire 10 that incorporates a disinfection light source 16, where the disinfection light source 16 by itself contains no intelligence or communication capability, such as one or more lamps (e.g., gas excimer lamps), LEDs or the like, etc. of any suitable type. However, the luminaire 10 includes a luminaire control circuit 12 implements the disinfection light exposure and dosage control protocol described herein.

Illumination lighting 19 output from the general illumination light source 18 of the luminaire 10 may carry information, such as a code (e.g. to identify the luminaire or its location) or downstream transmission of communication signaling and/or user data. The light based data transmission may involve modulation or otherwise adjusting parameters (e.g. intensity, color characteristic or distribution) of the illumination lighting 19 from the general illumination light source 18.

Terms such as "disinfection lighting device," "lighting device," or "lighting apparatus," as used herein, are intended to encompass essentially any combination of an example of a luminaire 10 discussed herein with other elements such as electronics and/or support structure, to operate and/or install the particular luminaire implementation. Such electronics hardware, for example, may include some or all of the appropriate driver(s) for the disinfection light source 16, any associated control processor or alternative higher level control circuitry, and/or data communication interface(s). The electronics for driving and/or controlling the lighting component(s) may be incorporated within the luminaire 10 or located separately and coupled by appropriate means to the light source component(s).

The term "coupled" as used herein refers to any logical, optical, physical or electrical connection, link or the like by which signals or light produced or supplied by one system element are imparted to another coupled element. Unless described otherwise, coupled elements or devices are not necessarily directly connected to one another and may be separated by intermediate components, elements or communication media that may modify, manipulate or carry the light or signals.

The direction of the arrows in the drawings, however, are for ease of illustration only. In actual implementations of the luminaire 10, the beams of the disinfection light 17 may be aimed in a variety of different directions, to facilitate optical processing by the various components discussed herein and/or to direct the disinfection light 17 output in a manner suitable to a particular application or installation. Also, the drawings show disinfection light 17 and illumination lighting 19 outputs from the luminaire 10 in a downward direction, for example, as if mounted to direct output light down from a ceiling, pedestal or lamp post through an illuminated volume toward a floor or an object surface 189 (e.g., work surface) or air positioned above the floor. It should be apparent that a luminaire 10 may be positioned in a variety of other orientations suitable for disinfection of a target pathogen 187 in a particular physical space 2, including surface(s) 188 and air 189 by a desired amount 140 (e.g., desired log reduction).

Reference now is made in detail to the examples illustrated in the accompanying drawings and discussed below. FIG. 1 is a block diagram of a disinfection lighting device (e.g., luminaire 10) that implements a disinfection light exposure and dosage limit control protocol. As shown, the luminaire 10 includes a disinfection light source 16 to emit a disinfection light 17, e.g., in a ultraviolet (UV) band for disinfecting a vicinity 180 of a physical space 2 of a target pathogen 187 that is exposed to the disinfection light 17. Generally, the UV band can cover the wavelength range 100-400 nanometers (nm), which is sub-divided into three bands: UVA (315-400 nm) UVB (280-315 nm) UVC (100-280 nm). In a first example, the UV band of the disinfection light 17 can be UVC spectrum between 200 nm to 230 nm wavelength. More specifically, the UV band of the disinfection light 17 can be UVC spectrum between approximately 207 nm to 230 nm. In another example, the UV band is approximately 222 nm or approximately 254 nm. In yet another example, the disinfection light 17 may be just outside of the UV band, such as the visible light spectrum between 405-430 nm.

Luminaire 10 includes a power supply 105 that is driven by a line power source 101 and optionally a non-line power source 102. A line power source 101 is referred to as grid power, wall power, and domestic power, alternating current (AC) electric power produced and delivered via AC mains to homes and businesses. Line power source 101 is the form of electrical power that consumers use when they plug in domestic appliances, televisions and electric lamps into wall outlets. Line power source 301 conveys line power (e.g., 120 volts alternating current (VAC), 244 VAC, or 277 VAC), sometimes referred to as "household power," "household electricity," "house current," "powerline," "domestic power," "wall power," "line power," "AC power," "city power," "street power" that is produced by an electric utility provider. Non-line power source 102 in the example is a battery, solar panel, or any other AC or DC source (e.g. a generator) that is not line powered.

Power supply 105 may include a magnetic transformer, electronic transformer, switching converter, rectifier, or any other similar type of circuit to convert an input power signal into a power signal suitable for a disinfection light source 16 and an optional general illumination light source 18. Luminaire 10 includes power distribution circuitry 125 driven by the line power source 101 or non-line power source 102. The power distribution circuitry 125 distributes power and ground voltages to the luminaire processor 130; luminaire memory 131; luminaire wireless radio communication interface system 155 (e.g., wireless transceivers); optional on-board occupancy, daylight, or audio sensor 45; and optional on-board pathogen sensor 48 to provide reliable operation of the various circuitry on the luminaire 10. Luminaire processor 130 includes a central processing unit (CPU) that controls the light source operation of the disinfection light source 16 and the optional general illumination light source 18. Luminaire memory 131 can include volatile and/or non-volatile storage.

In the case of luminaire 10, the disinfection light source 16 is configured to emit disinfection light 17 in a UV band for disinfecting a vicinity 180 of a space 2 of a target pathogen 187. The optional general illumination light source 18 is configured to emit illumination lighting 19 in the vicinity 180 of the physical space 2. The physical space 2 can include an office, hospital, medical facility, classroom, restaurant, retail store, restroom, and other private or public facilities.

Disinfection light source 16 can be an electrodeless UV lamp, such as a gas excimer lamp. An excimer lamp is a source of ultraviolet light produced by spontaneous emission of excimer molecules from an excited electronic state to the ground state. To excite emission of excimer molecules, an electric discharge that releases and transmits electricity in an applied electric field through a medium, such as a gas, can be utilized. The excimer lamp can include arc discharge light sources with a special chamber filled with noble gas, completely mercury-free, and without electrodes. One example disinfection light source 16 commercially available from Ushio America, Inc. is the Care222® UV disinfection module. The disinfection light source 16 can include filtered excimer lamps, which use a KrCL working excimer molecule, to generate 222 nm far-UVC light capable of inactivating a target pathogen 187, such as viruses and bacteria, on surface(s) 188 of various objects (e.g. desk, table, counter, chairs, etc.) and suspended in air 189. Disinfection light source 16 can emit intermittent pulses of the disinfection light 17 to reduce the target pathogen 187 on the surface 188 and suspended in air 189, and can include a short pass filter to filter out from the lamp the longer UV wavelengths that are harmful to a human 185. Other types of disinfection light sources 16 that are unfiltered are commercially available from High Energy Ozone LLC (HEO3), Sterilray™, and Eden Park Illumination, although these are examples of disinfection light sources 16 that are unfiltered. The disinfection light source 16 can be a disinfection light module that includes one or more disinfection light sources (e.g., one, two, three, four, or more excimer lamps). Commercially available lamps for illumination lighting 19 sometimes included coatings to block UV light. In one example, the disinfection light source 16 can be a commercially available xenon lamp that has the coatings that block UV light removed to allow the UV light to emanate out as the disinfection light 17.

Luminaire 10 further includes a driver circuit 11 coupled to control the disinfection light source 16 (e.g., lamp) to control light source operation of the disinfection light source 16. Driver circuit 11 can include an electrical circuit that pulses a high voltage to ignite or strike an arc of the disinfection light source 16, after which the discharge of the disinfection light source 16 can be maintained at a lower voltage. For example, the driver circuit 11 can include a ballast and an igniter, which can be wired in series with the disinfection light source 17 to control current flow through the gas medium of the disinfection light source 17. When the power is first switched on, the igniter/starter of the driver circuit 11 (which can be wired in parallel across the lamp) sets up a small current through the ballast and starter. This creates a small magnetic field within the ballast windings. A moment later, the starter interrupts the current flow from the ballast, which has a high inductance and therefore tries to maintain the current flow (the ballast opposes any change in current through it); it cannot, as there is no longer a circuit. As a result, a high voltage appears across the ballast momentarily, to which the lamp is connected; therefore the lamp receives this high voltage across it which strikes the arc within the tube/lamp. The driver circuit 11 will repeat this action until the lamp of the disinfection light source 16 is ionized enough to sustain the arc. When the lamp sustains the arc, the ballast of the driver circuit 11 performs its second function, to limit the current to that needed to operate the lamp of the disinfection light source 16. The lamp, ballast and igniter are typically rating-matched to each other; these parts are typically replaced with the same rating as the failed component to ensure proper operation.

Disinfection light source 16 and the optional general illumination light source 18 may include electrical-to-optical transducers, such as various light emitters. The emitted disinfection light 17 may be in the UV spectrum in the case of the disinfection light source 16, the visible spectrum for the illumination lighting 19 emitted from the general illumination light source 18, or in other wavelength ranges. Suitable light generation sources include various conventional lamps, such as incandescent, fluorescent or halide lamps; one or more light emitting diodes (LEDs) of various types, such as planar LEDs, micro LEDs, micro organic LEDs, LEDs on gallium nitride (GaN) substrates, micro nanowire or nanorod LEDs, nanoscale LEDs, photo pumped quantum dot (QD) LEDs, micro plasmonic LED, micro resonant-cavity (RC) LEDs, and micro photonic crystal LEDs; as well as other sources such as micro super luminescent Diodes (SLD) and micro laser diodes. A luminaire 10 that includes a laser diode as the disinfection light source 16 can include a light frequency up-converter to convert original light produced from the laser diode via second, third, or fourth harmonic light generation into disinfection light 17 (of a shorter wavelength) to deactivate a target pathogen 187. Examples of such a light frequency up-converter to emit disinfection light 17 (e.g., UV light) from converted original light (e.g., visible light) from the laser diode are disclosed in U.S. Patent Pub. No. 2020/0073199, published Mar. 5, 2020, titled "Light Frequency Upconversion of Laser Light, for Cleansing," the entirety of which is incorporated by reference herein. Of course, these light generation technologies are given by way of non-limiting examples, and other light generation technologies may be used. For example, it should be understood that non-micro versions of the foregoing light generation sources can be used.

A lamp or "light bulb" is an example of a single light source. An LED light engine may use a single output for a single source but typically combines light from multiple LED type emitters within the single light engine. Disinfection light source 16 can include a module of multiple gas excimer lamps and LEDs to emit the disinfection light 17. Optional general illumination light source 18 can include light emitting diodes (LEDs) that emit red, green, and blue (RGB) light or tunable white light to emit the illumination lighting 19. Many types of light sources provide uniform light output, although there may be some intensity striations. For purposes of the present examples, however, the light source output may not be strictly uniform across the output area or aperture of the source. For example, although the source may use individual emitters or groups of individual emitters to produce the light generated by the overall source; depending on the arrangement of the emitters and any associated mixer or diffuser, the light output may be relatively uniform across the aperture. The individual emitters or groups of emitters may be separately controllable, for example to control intensity of the source output.

Driver circuit 11 can also be coupled to the optional general illumination light source 18. Driver circuit 11 can drive the disinfection light source 16 and/or the optional general illumination light source 18 by regulating the power to disinfection light source 16 and the optional general illumination light source 18 by providing a constant quantity or power to the disinfection light source 16 and the optional general illumination light source 18 as their electrical properties change with temperature, for example. The driver circuit 11 provides power to disinfection light source 16 and the optional general illumination light source 18. As noted above, the driver circuit 11 may include a ballast and an igniter for an arc gaslamp type of disinfection light source 16. Alternatively or additionally, driver circuit 11 can include a constant-voltage driver, constant-current driver, or AC LED driver type circuit that provides dimming through a pulse width modulation (PWM) circuit and may have many channels for separate control of different LEDs or LED arrays that comprise the optional general illumination light source 18 or even a disinfection light source 16 formed of LEDs. An example of a commercially available driver circuit 11 is manufactured by EldoLED®. In the case of luminaire 10, the driver circuit 11 is coupled to the disinfection light source 16 and the optional general illumination light source 18 to control light source operation of the disinfection light source 16 and the optional general illumination light source 18.

Driver circuit 11 can further include an AC or DC current source or voltage source, a regulator, an amplifier (such as a linear amplifier or switching amplifier), a buck, boost, or buck/boost converter, or any other similar type of circuit or component. Driver circuit 11 may output a variable voltage or current to the disinfection light source 16 and the optional general illumination light source 18 that may include a DC offset, such that its average value is nonzero, and/or an AC voltage.

In order to advantageously reduce a physical size of a rectifier (AC-DC converter), e.g., included in the power supply 105 or the driver circuit 11, the luminaire 10 can include a plurality of disinfection light sources 16A-N (e.g., two, three, four, or more). Execution of the exposure and dosage control programming 132, controls, via the driver circuit 11, the plurality of disinfection light sources 16A-N, such that the plurality of periods 137A-N (e.g., on cycles) of the dose cycle 136 are divided among the plurality of disinfection light sources 16A-N in a sequential fashion. For example, if there are two disinfection light sources 16A-B, then a first disinfection light source 16A can be driven on for a first period 137A (e.g., 31 seconds) and the second disinfection light source 16B can be driven on for a second period 137B (e.g., 31 seconds). In a third period 137C, the first disinfection light source 16A is driven on again and in a fourth period 137D the second disinfection light source 16B is driven on again. Splitting the periods 137A-N (e.g., on cycles) of the dose cycle 136 across a plurality of disinfection light sources 16A-N that are sequentially driven, enables the disinfection light sources 16A-N to have lower power requirements, which means the rectifier (e.g., included in the power supply 105 or the driver circuit 11) can have a smaller form factor. Two disinfection light sources 16A-B that require 15 Watts of power each are equivalent to a single disinfection light source 16 that requires 30 Watts.

By driving the two disinfection light sources 16A-B that are 15 Watts sequentially and doubling the plurality of periods 137A-N, the same target pathogen UV radiation level 139 can be achieved as the single disinfection light source 16 that is 30 Watts. Having the plurality of disinfection light sources 16A-B reduces the physical size of the rectifier and thereby lowers production cost of the luminaire 10.

Luminaire 10 includes a luminaire control circuit 12, for example, to modulate pulses of the disinfection light 17 emitted from the disinfection light source 16 at an appropriate dose, for example, to operate within American Conference of Governmental Industrial Hygienists (ACGIH) safety guidelines of an ultraviolet radiation threshold limit 133. The luminaire control circuit 12 includes a luminaire processor 130 coupled to the driver circuit 11 and configured to control the disinfection light source 16 via the driver circuit 11. Luminaire control circuit 12 further includes a luminaire memory 131 accessible to the luminaire processor 130.

As shown, the luminaire memory 131 includes a UV radiation threshold limit 133 for safe exposure of a human 185 to the UV band over a predetermined dose period 134. Luminaire memory 131 further includes a total UV radiation threshold exposure level 135 over a dose cycle 136 of the vicinity 180. The dose cycle 136 corresponds to the predetermined dose period 134 or is a fraction or multiple thereof. Luminaire memory 131 further includes a target pathogen UV radiation level 139 that is sufficient to reduce the target pathogen 187 by a desired amount 140, e.g., a desired logarithmic (log) reduction, in the vicinity 180 over the predetermined dose period 134. The desired log reduction can specify the desired amount 140 of reduction of the target pathogen 187. For example, desired log reduction is a 0-log reduction is no reduction of the target pathogen 187 from the original concentration, while a 1-log reduction corresponds to a reduction of 90% of the target pathogen 187, a 2-log reduction corresponds to a reduction of 99% percent of the target pathogen 187, a 3-log reduction corresponds to a reduction of 99.9% of the target pathogen 187, and a 4-log reduction corresponds to a reduction of 99.99% of the target pathogen.

Luminaire memory 131 further includes exposure and dosage control programming 132 to implement the disinfection light exposure and dosage limit control protocol described herein. Execution of the exposure and dosage control programming 132 by the luminaire processor 130 configures the luminaire 10 to perform the following functions. First, the luminaire 10 initiates the dose cycle 136 of the vicinity 180 in which the disinfection light source 16 emits the disinfection light 17 continuously or during a plurality of periods 137A-N of the dose cycle 136 by recording a beginning time 138 of the dose cycle 136. The plurality of periods 137A-N of the dose cycle 136 are lengths of time that the disinfection light source 16 is turned on to the emit disinfection light 17. Second, the luminaire 10 controls, via the driver circuit 11, the disinfection light source 16 over the dose cycle 136 to emit the disinfection light 17 continuously or during the plurality of periods 137A-N for disinfecting the vicinity 180 to substantially obtain the target pathogen UV radiation level 139 and restrict the total UV radiation threshold exposure level 135 by the UV radiation threshold limit 133.

For example, assume the UV radiation threshold limit 133 is 22 millijoules per centimeter squared (mJ/cm$^2$) over a predetermined dose period 134 of 8 hours (hr) and the UV band of disinfection light 17 is approximately 222 nm. Assume the target pathogen UV radiation level 139 is 24 mJ/cm$^2$ to deactivate many common pathogens of concern and a desired on time for the disinfection light source 16 is 75 minutes a day. Then, in a dose cycle 136 that is 24 hours, this results in a total UV radiation threshold exposure level 135 of 66 mJ/cm$^2$ on the head of the human 185 and 27.5 mJ/cm$^2$ on the surface 188. In the example, the total UV radiation threshold exposure level 135 is also not exceeded in any one eight-hour period during the 24-hour dose cycle 136. This total UV radiation threshold exposure level 135 is based on the following assumptions: the human 185 is 6 feet 2 inches individual (95 percentile of height of a male in the United States); the surface 188 is tabletop that is 3 feet above the floor; the luminaire 10 is mounted on a 9 foot ceiling; and the reflectance of the surface 188, ceiling, and walls of the vicinity 180 is approximately 5%.

This results in emission of 22 mJ/cm$^2$ over the plurality of periods 137A-N of the dose cycle 136. This means for every 75 minutes per day, the disinfection light source 16 is on approximately 31.25 seconds for every 10 minutes or 15.625 seconds for every 5 minutes. The on time of the disinfection light source 16 and number of periods 137A-N is controlled by the exposure and dosage control programming 132 and can also factor in the typical rated lifetime limit 145 (e.g., 3,000 hours) of the disinfection light source 16 to maximize a desired calendar life (e.g., 5 years) of the disinfection light source 16. Based on the foregoing discussion, it should be understood that the UV radiation threshold limit 133 is adjustable and depends on the UV band of the disinfection light 17 and assumptions regarding the size or stature of the human 185; height/position of the surface 188; mounting location of the luminaire 10; and reflectance of the surface 188, ceiling, and walls of the vicinity 180. The target pathogen UV radiation level 139 is also adjustable and depends on the target pathogen 187 of concern.

The function to control, via the driver circuit 11, the disinfection light source 16 over the dose cycle 136 includes functions to: (a) emit the disinfection light 17 for disinfecting the vicinity 180, (b) track an elapsed time 141 of the dose cycle 136 based on the beginning time 138, (c) adjust the total UV radiation threshold exposure level 135 based on the emission of the disinfection light 17 continuously or during the plurality of periods 137A-N, (d) determine whether the total UV radiation threshold exposure level 135 falls below or exceeds the UV radiation threshold limit 133, and (e) determine whether the total UV radiation threshold exposure level 135 falls below or exceeds the target pathogen UV radiation level 139.

In a first example where the dosage limit of disinfection light 17 is not reached, the function to control, via the driver circuit 11, the disinfection light source 16 over the dose cycle 136 includes further functions to: (f) in response to determining that the total UV radiation threshold exposure level 135 falls below the UV radiation threshold limit 133 and falls below the target pathogen UV radiation level 139, repeat functions (a) to (e).

In a second example where the dosage limit of disinfection light 17 is reached, the function to control, via the driver circuit 11, the disinfection light source 16 over the dose cycle 136 further includes functions to: (g) in response to determining that the total UV radiation threshold exposure level 135 exceeds the UV radiation threshold limit 133 or the target pathogen UV radiation level 139, end the dose cycle 136 by disabling emission of the disinfection light 17 for disinfecting the vicinity 180 based on the elapsed time 141 of the dose cycle 136 and the predetermined dose period 134.

Figure 2:
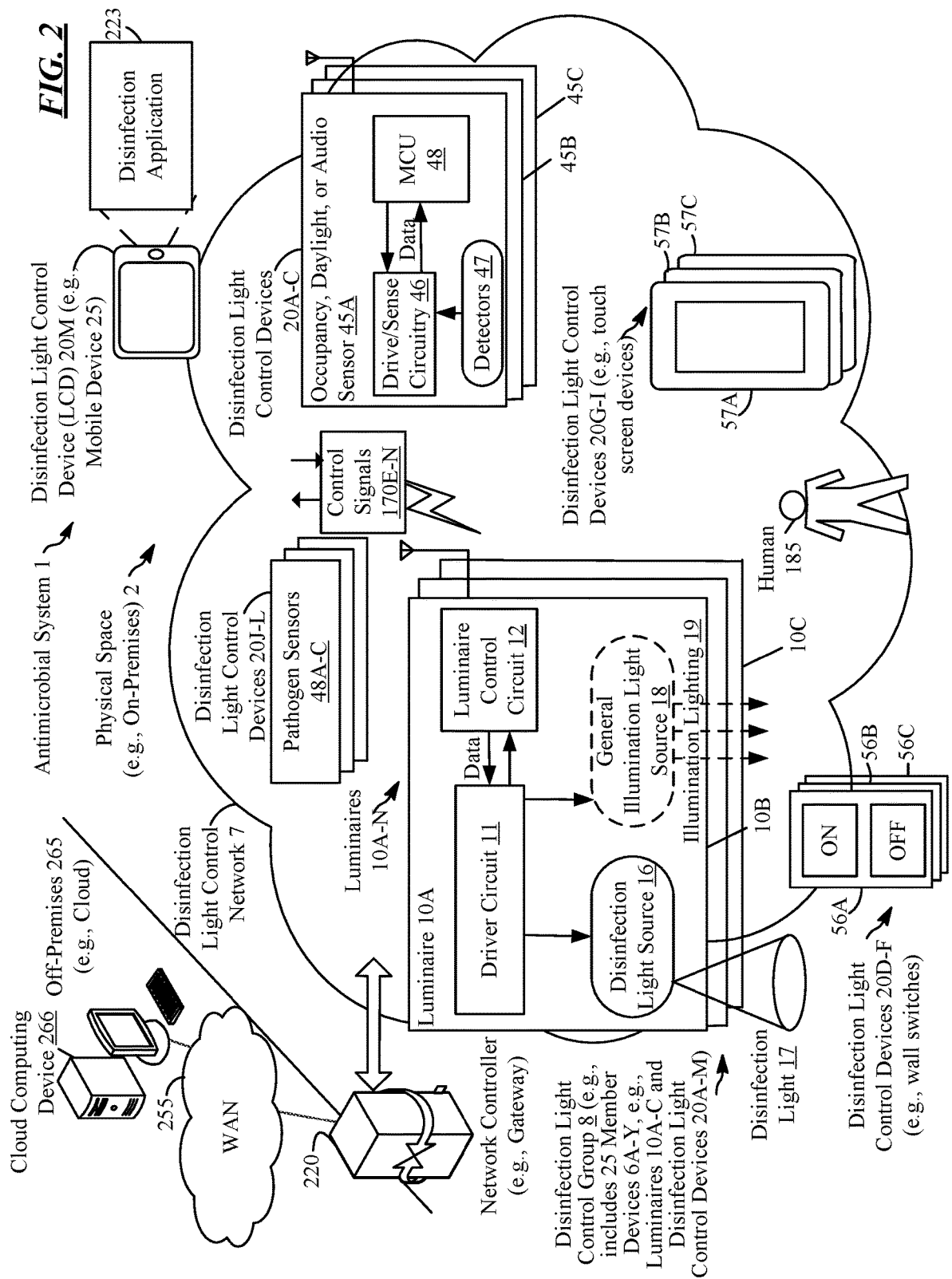
FIG. 2 is a high-level functional block diagram of an example of an antimicrobial system that includes thirteen luminaires like that of FIG. 1 and twelve disinfection light control devices.

As further shown in FIG. 1, the luminaire 10 can optionally include integrated disinfection light control devices (LCDs) 20A, 20J. The disinfection light control device 20 generates a control signal 170 to control emission of a disinfection light 17 in an ultraviolet (UV) band for disinfecting a vicinity 180 of a physical space 2 of a target pathogen 187. Alternatively or additionally, as shown in FIG. 2, the luminaire 10 can be coupled (e.g., via a wired or wireless disinfection light control network 7) to various disinfection light control devices 20A-M.

Returning to FIG. 1, disinfection light control device 20A is an occupancy, daylight, or audio sensor 45 and disinfection light control device 20J is a pathogen sensor 48. The drive/sense circuitry 46 and detectors 47 of the occupancy, daylight, or audio sensor 45 are shown as on-board the luminaire 10. Detectors 47 can be an occupancy sensor (e.g., infrared sensor or image sensor, such as a camera, for occupancy or motion detection), an in-fixture daylight sensor, an audio sensor, a temperature sensor, or other environmental sensor. Drive/sense circuitry 46, such as application firmware, drives the occupancy, audio, and photo sensor hardware.

In an example where the disinfection light control device 20 controls emission of disinfection light 17, execution of the exposure and dosage control programming 132 by the luminaire processor 130 configures the luminaire 10 to perform the following functions. First, luminaire 10 receives the control signal 170 from the disinfection light control device 20. Second, in response to receiving the control signal 170, the luminaire 10 controls, via the driver circuit 11, the disinfection light source 16 over the dose cycle 136 to emit the disinfection light 17 for disinfecting the vicinity 180 to substantially obtain the target pathogen UV radiation level 139 and restrict the total UV radiation threshold exposure level 135 by the UV radiation threshold limit 133.

Hence, control of the disinfection light source 16 can be tied to occupancy via a first control (e.g., sensing) signal 170A from the occupancy sensor 45 that indicates occupancy of the vicinity 180 by a human 185. The disinfection light control device 20A includes detectors 47 (e.g., an occupancy detector 45). Occupancy sensor 45 can be a passive infrared sensor, active infrared sensor, image sensor (e.g., visible light camera) that captures images and subsequently processes the captured image to detect the human 185. The control signal 170 includes a first sensing signal 170A from the occupancy detector 45 that indicates the human 185 is present in the vicinity 180. An elapsed time 141 of the dose cycle 136 tracks only when the human 185 is present in the vicinity 180. The function to restrict the total UV radiation threshold exposure level 135 by the UV radiation threshold limit 133 includes the following. First, the luminaire 10 tracks the elapsed time 141 of the dose cycle 136 as a sum of a plurality of time durations 144A-N that the human 185 is present in the vicinity 180 while the disinfection light 17 is emitted from the disinfection light source 16. Second, the luminaire 10 determines the total UV radiation threshold exposure level 135 across the plurality of time durations 144A-N. Third, the luminaire 10 determines that the total UV radiation threshold exposure level 135 is approaching the UV radiation threshold limit 133. Fourth, in response to determining that the total UV radiation threshold exposure level 135 is approaching the total UV radiation threshold limit 133, the luminaire 10 disables emission of the disinfection light 17 from the disinfection light source 16 while the human 185 is present in the vicinity 180.

In another occupancy sensing example, the first sensing signal 170A inhibits transmission of UV type of disinfection light 17 if the human 185 is present. If the first sensing signal 170A indicates the vicinity 180 is unoccupied, the disinfection light source 16 can be controlled to accelerate emission of a desired dose of disinfection light 17, e.g. 24 mJ/cm$^2$ as a super dose level 142 during an accelerated super dose time period. If the first sensing signal 170A indicates the vicinity 180 is occupied, then the 24 mJ/cm$^2$ is emitted during a standard dose cycle 136 with a much longer time period compared to the accelerated super dose time period of the super dose level 142. Additionally, if the first sensing signal 170A indicates no human 185 has entered the vicinity 180 since the end of the standard dose cycle 136 or emission of the super dose level 142, then there may be no need for further disinfection of the vicinity 180. Such a control technique can advantageously extend a lifetime of the disinfection light source 16 and save energy. Alternatively, based on the first sensing signal 170A, if the physical space 2 is a large room like a store, it can be desirous to know if the human 185 is in a specific vicinity 180A of a plurality of vicinities 180A-D (e.g., FIG. 3) so as to only disinfect the specific vicinity 180A. Hence, only the disinfection light source 180A of the luminaire 10A where the human 185 is turned on to emit disinfection light 17 to disinfect the specific vicinity 180A while the human 185 is actually present and shortly thereafter occupying the vicinity 180A.

Control of the disinfection light source 16 can be tied to a pathogen sensor 48 present in the vicinity 180. The pathogen sensor 48 can be located in the vicinity 180 or outside the vicinity 180 in a heating, ventilation, and air conditioning system (HVAC). The spectrometer 49 can utilize Raman spectroscopy to examine light absorption or laser light to excite the examined surface(s) 188 of objects in the physical space 2 and the target pathogen 187 to a quasi-excited state. The fluorescence of the surface 188 from one atomic state to another is then examined, and based on Raman spectroscopy, the target pathogen 187 can be detected, e.g., by analyzing carbon dioxide, oxygen, humidity, temperature, etc. Machine learning be used to detect a specific type of target pathogen 187 (e.g., virus).

With a robust pathogen sensor 48, the vicinity 180 can be disinfected when a target pathogen 187 is detected. Examples of luminaires incorporating a pathogen sensor 48 with a spectrometer 49 for pathogen detection are disclosed in U.S. Pat. No. 10,281,326, issued May 1, 2019, titled "Fixture that Provides Light Incorporating a Reconfigurable Spectrometer"; and U.S. Pat. No. 10,458,844, issued Oct. 29, 2019, titled "Reconfigurable Optical Fiber Spectrometer in a Lighting Device," the entireties of which are incorporated by reference herein.

In this example, disinfection light control device 20J includes the pathogen sensor 48. The control signal 170 includes a second sensing signal 170B from the pathogen sensor 48 indicating that the target pathogen 187 is present in the vicinity 180. The pathogen sensor 48 includes a spectrometer 49 and a sense circuit 50. The sense circuit 50 includes a pathogen sensor processor 730 configured to control the spectrometer 49, a pathogen sensor memory 731 accessible to the pathogen sensor processor 730 and storing spectral reference data 752 of the target pathogen 187, and pathogen sensor programming 751 in the pathogen sensor memory 731. Execution of the pathogen sensor programming 751 by the pathogen sensor processor 730 configures the pathogen sensor 48 to perform the following functions. First, the pathogen sensor 48 generates, via the spectrometer 49, a spectral power measurement 753 for the vicinity 180 by detecting, via the spectrometer 49, light passed, reflected, or shifted and regenerated by the target pathogen 187.

Second, the pathogen sensor 48 analyzes, via the sense circuit 50, the spectral power measurement 753 against spectral reference data 752 (e.g., a spectral power distribution) to generate the second sensing signal 170B indicating whether the target pathogen 187 is present in the vicinity 180. This analysis compares the spectral power measurement 753 with the spectral reference data 752 to determine the presence of any target pathogen 187, but may also determine a specific target pathogen identifier 754 of the target pathogen 187. The spectrometer 49 can be a Raman spectrometer, and other types of suitable spectrometers can be used.

Super dosing of the vicinity may occur, for example, if a human 185 is not in the vicinity 180 or if the target pathogen 187 is detected in the vicinity 180. In this example, the control signal 170 includes either the first sensing signal 170A from the occupancy detector 45 that indicates the human 185 is not present in the vicinity 180 or the second sensing signal 170B from the pathogen sensor 48 indicates that the target pathogen 187 is present in the vicinity 180. Hence, the function to control, via the driver circuit 11, the disinfection light source 16 over the dose cycle 136 to emit the disinfection light 17 includes to: in response to receiving control signal 170, increase the emission of the disinfection light 17 for disinfection the vicinity 180 to a super dose level 142 to accelerate deactivation of the target pathogen 187 such that the UV radiation threshold limit 133 is exceeded over the predetermined dose period 134.

As shown in FIGS. 1-2, a super dose level 142 can be emitted from the disinfection light source 16 in response to a control signal 170 from other types of disinfection light control devices 20D-I, such as a button being pushed on wall switches 56A-C or touch screen devices 57A-C. For example, the human 185 can activate the super dose level 142 with a button after visually verifying no humans are in the vicinity 180 (e.g., room). An occupancy sensor 45 and the button are thus used an extra safety margin to avoid the human 185 being exposed to the disinfection light 17. For example, the super dose level 142 can be activated automatically when the vicinity 180 is unoccupied based on the first sensing signal 170A from the occupancy sensor 45 or based on a fourth control signal that is a defined time of day 170D. The super dose level 142 can be activated automatically in response to the detection of the target pathogen 187 by the pathogen sensor 48 and when the vicinity 180 is detected as being unoccupied by the occupancy sensor 45. The super dose level 142 can be activated automatically in response to the detection of target pathogen 187 and the vicinity 180 being unoccupied, but then not activated during the dose cycle 136 unless the vicinity 180 is occupied by the human 185 again.

Without active cooling, the luminaire 10, including the disinfection light source 16 and the driver circuit 11, may possibly overheat. To safely emit a super dose level 142, the disinfection light source 16 may be turned off periodically for cooling during a dose cycle 136 of the super dose level 142. For example, the dose cycle 136 of the super dose level 142 may be 21 minutes total and include 15 minutes total on time and 6 minutes total off time. Hence, in the example, the dose cycle 136 of the disinfection light source 16 alternates between three periods 137A-C (e.g., on cycles) that are 5 minutes each and three off cycles that are 2 minutes each during the dose cycle 136. Additionally, in some examples, the luminaire 10 can include a thermocouple (not shown) to measure a temperature of critical components of the luminaire 10, including the disinfection light source 16 and the driver circuit 11. If the measured temperature exceeds a temperature threshold (not shown) stored in the luminaire memory 131, the disinfection light source 16 can be turned off by the exposure and dosage control programming 132. This technique can be generally utilized in the light exposure and dosage control protocol procedure described herein, but is particularly applicable to the super dose level 142.

Compensation for depreciation of the disinfection light source 16 can be employed, for example, if the disinfection light 17 output slowly decreases over time. Although one technique to compensate for depreciation is to increase the intensity of the disinfection light 17, such a technique can damage the disinfection light source 16 and adversely affect a rated lifetime limit 145 and a calendar life of the disinfection light source 16. Hence, to compensate for depreciation of the disinfection light source 16, the luminaire 10 increases the on time as the disinfection light source 16 depreciates over time. The luminaire memory 131 includes a total disinfection light source on time 143 that specifies a cumulative on time that the disinfection light 17 is emitted from the disinfection light source 16 over a lifetime of the disinfection light source 16.

In the depreciation compensation example, execution of the exposure and dosage control programming 132 by the luminaire processor 130 configures the luminaire 10 to perform functions, including functions to: monitor each time duration 144A-C of past periods 137A-C of the dose cycle 136 that the disinfection light source is on; update the total disinfection light source on time 143 based on the monitored time durations 144A-C; and adjust future periods 137D-N of the dose cycle 136 based on the total disinfection light source on time 143. If the disinfection light source 16 becomes dimmer over the monitored time durations 144A-C, then the adjustment increases a length of the future periods 137D-N. This is achieved by establishing the disinfection light source 16 depreciation vs. on time relationship function (e.g., which can be linear, curved, etc.) and then increasing the on time (e.g., length of the future periods 137D-N of dose cycle 136) to account for the depreciation of the disinfection light source 16. If the disinfection light source 16 depreciation relationship is +10%, then the disinfection light source 16 is turned on for 10% longer, e.g., the length of period 137D of the dose cycle becomes 10% longer. For example, the on time is initially 31.25 seconds every 10 minutes in periods 137A-C, but becomes 34.375 seconds for every 10 minutes in subsequent periods 137D-N. Alternatively, if the disinfection light source 16 becomes brighter over the monitored time durations 144A-C of past periods 137A-C, then the adjustment decreases the on time of future periods 137D-N. If the disinfection light source 16 depreciation relationship is −5%, then the disinfection light source 16 is turned on 5% less, e.g., the length of period 137D of the dose cycle becomes 5% shorter. For example, the on time is initially 30 seconds every 10 minutes in periods 137A-C, but becomes 28.5 seconds for every 10 minutes in subsequent periods 137D-N.

Depreciation compensation can also be applied to the super dose level 142. For example, the luminaire memory 131 includes a total disinfection light source on time 143 that specifies a cumulative on time that the disinfection light 17 is emitted from the disinfection light source 16 over a lifetime. The function to control, via the driver circuit 11, the disinfection light source 16 over the dose cycle 136 to emit the disinfection light 17 includes to: based on the total disinfection light source on time 143, adjust a super dose time period of the super dose level 142 to compensate for depreciation of the disinfection light source 16. The super dose time period of the super dose level 142 is different earlier in the lifetime of the disinfection light source 16 compared to later in the lifetime of the disinfection light source 16. For example, if the disinfection light source 16 becomes dimmer over time and the disinfection light source 16 depreciation relationship is +10%, then the disinfection light source 16 is turned on for 10% longer, e.g., the super dose time period increases and becomes 10% longer. Alternatively, if the disinfection light source 16 becomes brighter over time and the depreciation relationship is −5%, then the super dose time period decreases by 5%.

A failure check can be implemented in the exposure and dosage control programming 132 to ensure the disinfection light source 16 is running properly. For example, a voltage and a current of the driver circuit 11 and/or the disinfection light source 16 can be monitored by the exposure and dosage control programming 132. In addition, an optical sensor (not shown) can be incorporated into the luminaire 10 or elsewhere in the antimicrobial system 1 to ensure the disinfection light source 16 is on at an appropriate intensity level. The optical sensor can be a UV sensor or a visual sensor that monitors the fluorescence and a measured intensity level of the fluorescence of the disinfection light source 16 (e.g., in the glass) against a normal intensity range (not shown) or a normal fluorescence range (not shown) that are stored in the luminaire memory 131 to check whether the disinfection light source 16 is running properly or has failed.

If the luminaire 10 is installed in an outdoor type of physical space 2, e.g., where the vicinity is 180 is located outdoors, then the exposure and dosage control programming 132 can implement techniques to save energy and extend a lifetime of the disinfection light source 16. Direct sunlight is a known disinfectant and has optical disinfectant properties. Hence, in the outdoor vicinity 180, the exposure and dosage control programming 132 turns the disinfection light source 16 off when a first control signal 170A indicates the outdoor vicinity 180 is bathed in direct sunlight, e.g., based on a first sensing signal 170A received from a daylight sensor 45. When the first sensing signal 170A received from the daylight sensor 45 indicates the outdoor vicinity 180 is no longer being bathed in sunlight and is dark, e.g., the sun is obscured by clouds or at low angles, then the exposure and dosage control programming 132 operates the disinfection light source 16 of the luminaire 10 in accordance with the dosage and limit controls described herein.

As shown, luminaire processor 130 is optionally coupled to a luminaire communication interface system 155 for receiving and transmitting various control signals 170E-N for disinfection light 17. Luminaire communication interface system 155 of FIG. 1, sensor communication interface system 655 of FIGS. 6-7, and disinfection LCD communication interface system 855 of FIGS. 8A-B allow for data communication (e.g., wired or wireless) over various networks, including the disinfection light control network 7 of FIGS. 2-3. Communication interface systems 155, 655, 855 include at least one radio frequency (RF) transceiver (XCVR), for example, a single-band, dual-band, or tri-band chipset of RF transceiver(s) 156A-B configured for wireless communication via separate radios that operate at three different frequencies, such as sub-GHz (e.g., 900 MHz), Bluetooth Low Energy (BLE) (2.4 GHz), and 5 GHz, for example. For example, luminaire communication interface system 155 of luminaire 10A includes a first luminaire RF transceiver 156A configured for wireless communication (e.g., unicast and multicast) via a wireless disinfection light control network 7 over a first wireless disinfection light control network communication band (e.g., sub-GHz) for lighting control and systems operations (or information), such as control signals 170E-N for disinfection light 17, with member devices 6B-Y (e.g., luminaires 10B-N and disinfection light control devices 20A-M) of the disinfection light control group 8. Wireless radio communication interface system 155 can include a second luminaire wireless RF transceiver 156B for communication (e.g., point-to-point) via a commissioning network (not shown) with the disinfection light control devices 20M (e.g., mobile device 25) over a second different wireless commissioning network communication band, such as 1 GHz or above communications (e.g., 2.4 GHz for Bluetooth) for commissioning, configuration, or maintenance operations. Luminaire 10 can communicate over an optional secondary network (e.g., wired or wireless LAN) via the second luminaire wireless RF transceiver 156B, such as a backhaul network for communication between the luminaires 10A-N, disinfection light control devices 20A-M, and a network controller (e.g., gateway) 220. Transport layer methods ride on the network layer function of the RF transceivers 156A-B. The second luminaire RF transceiver 156B is optional. As further shown, luminaire communication interface system 155 can include an optional wired network communication interface 157 for communication over a wired disinfection light control network 7.

Figure 6:
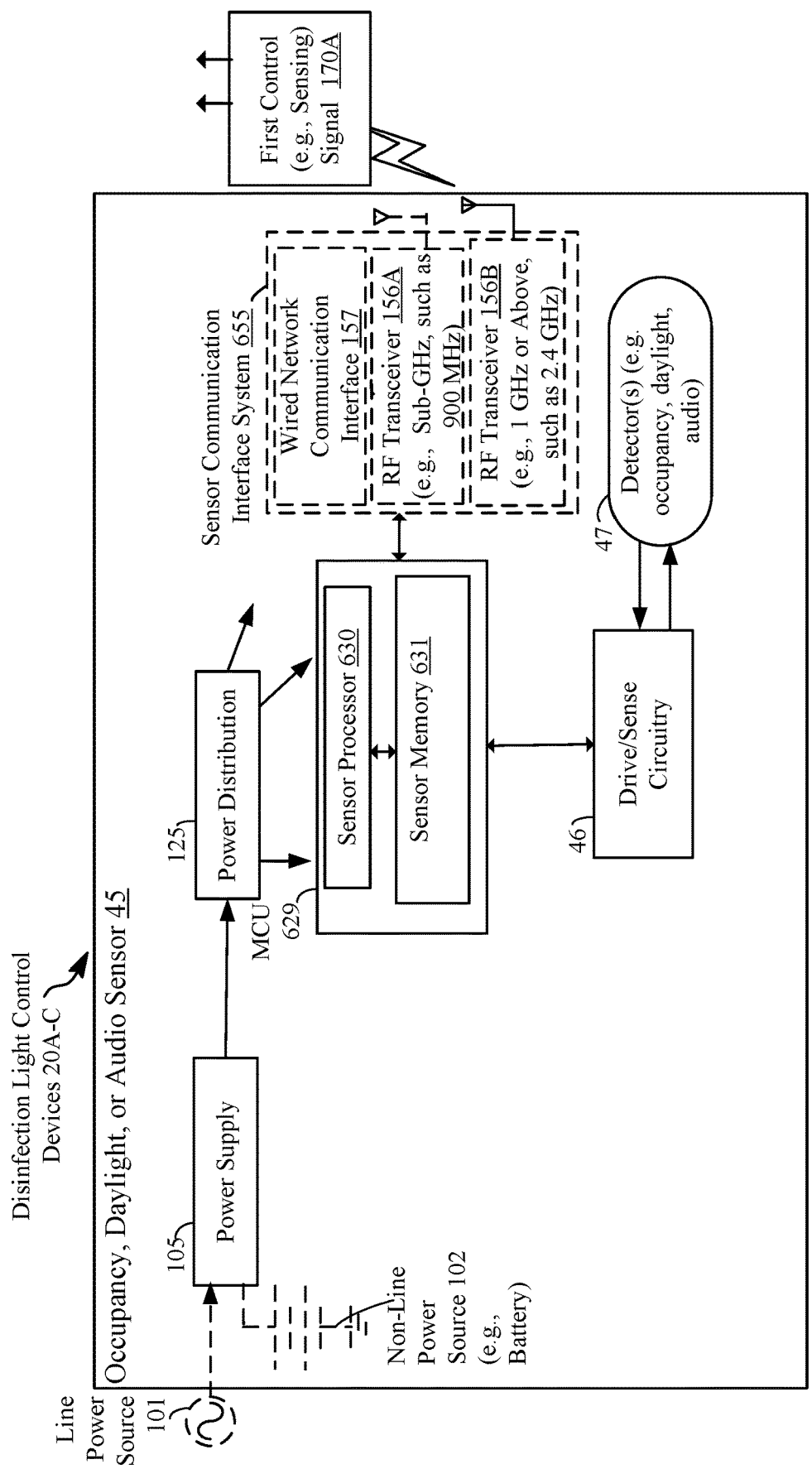
FIG. 6 is a block diagram of a disinfection light control device that is an occupancy, audio, or daylight sensor.
Figure 7:
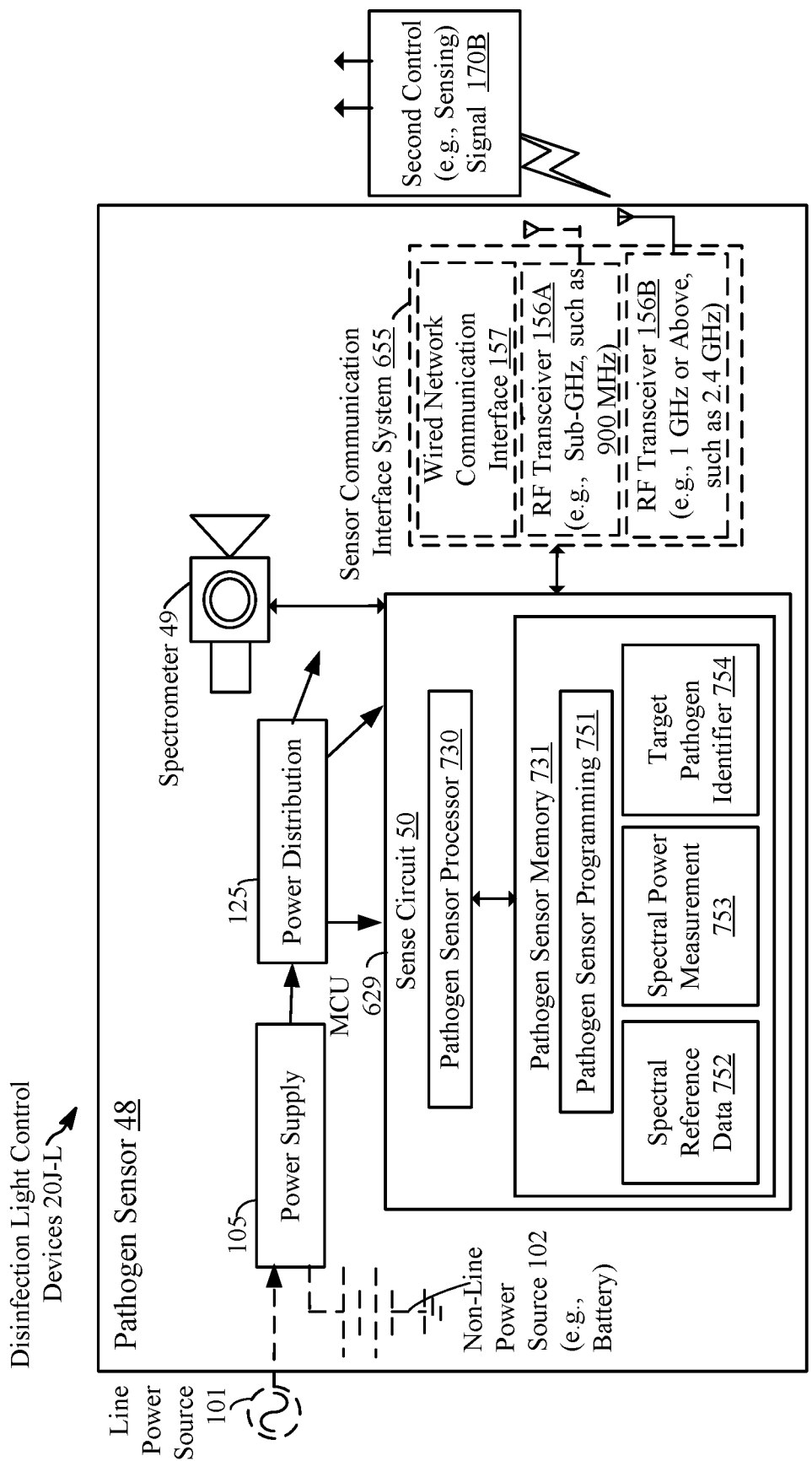
FIG. 7 is a block diagram of a disinfection light control device that is a pathogen sensor.
Figure 8A:
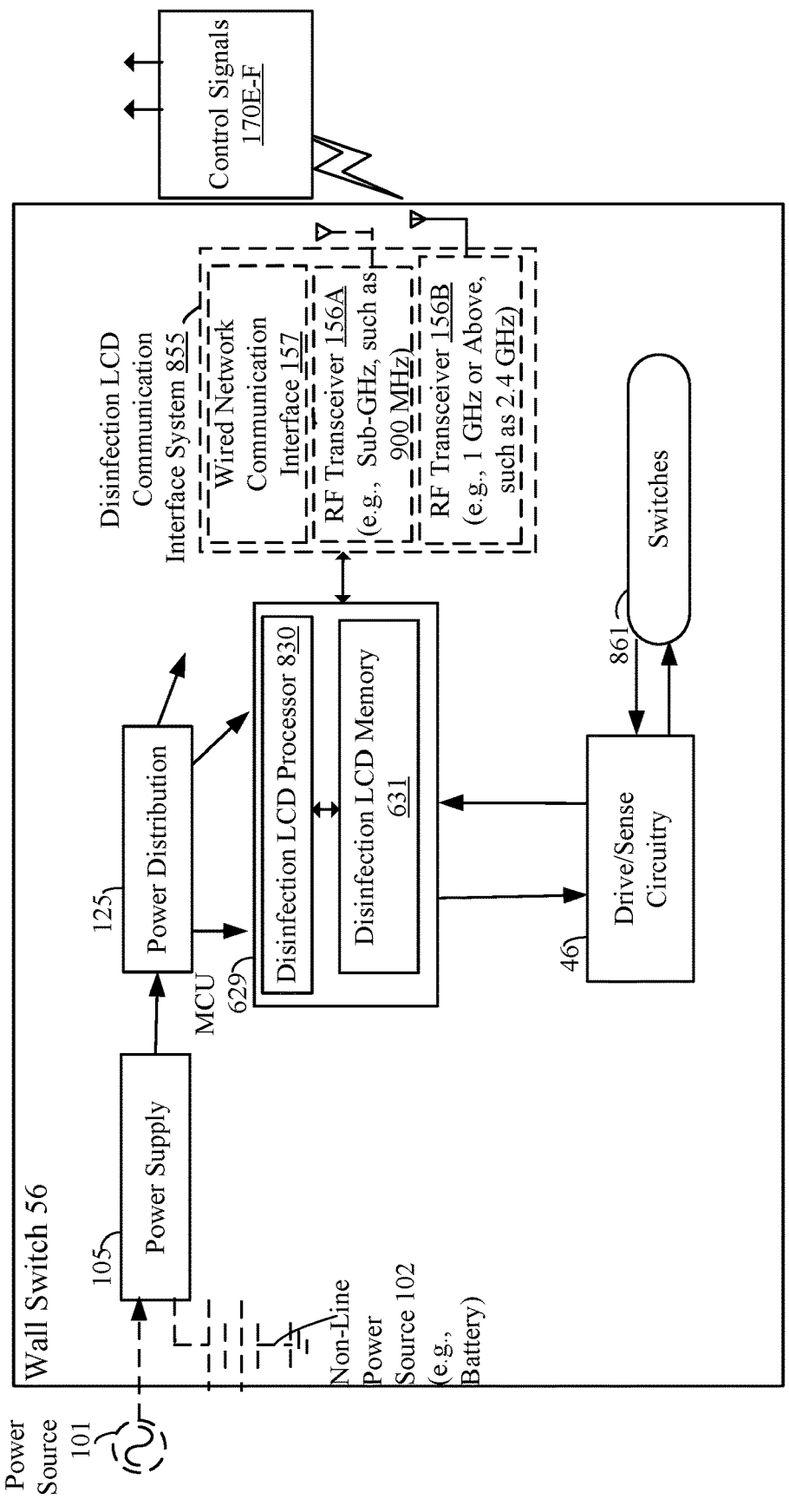
FIG. 8A is a block diagram of a disinfection light control devices that is a wall switch.
Figure 8B:
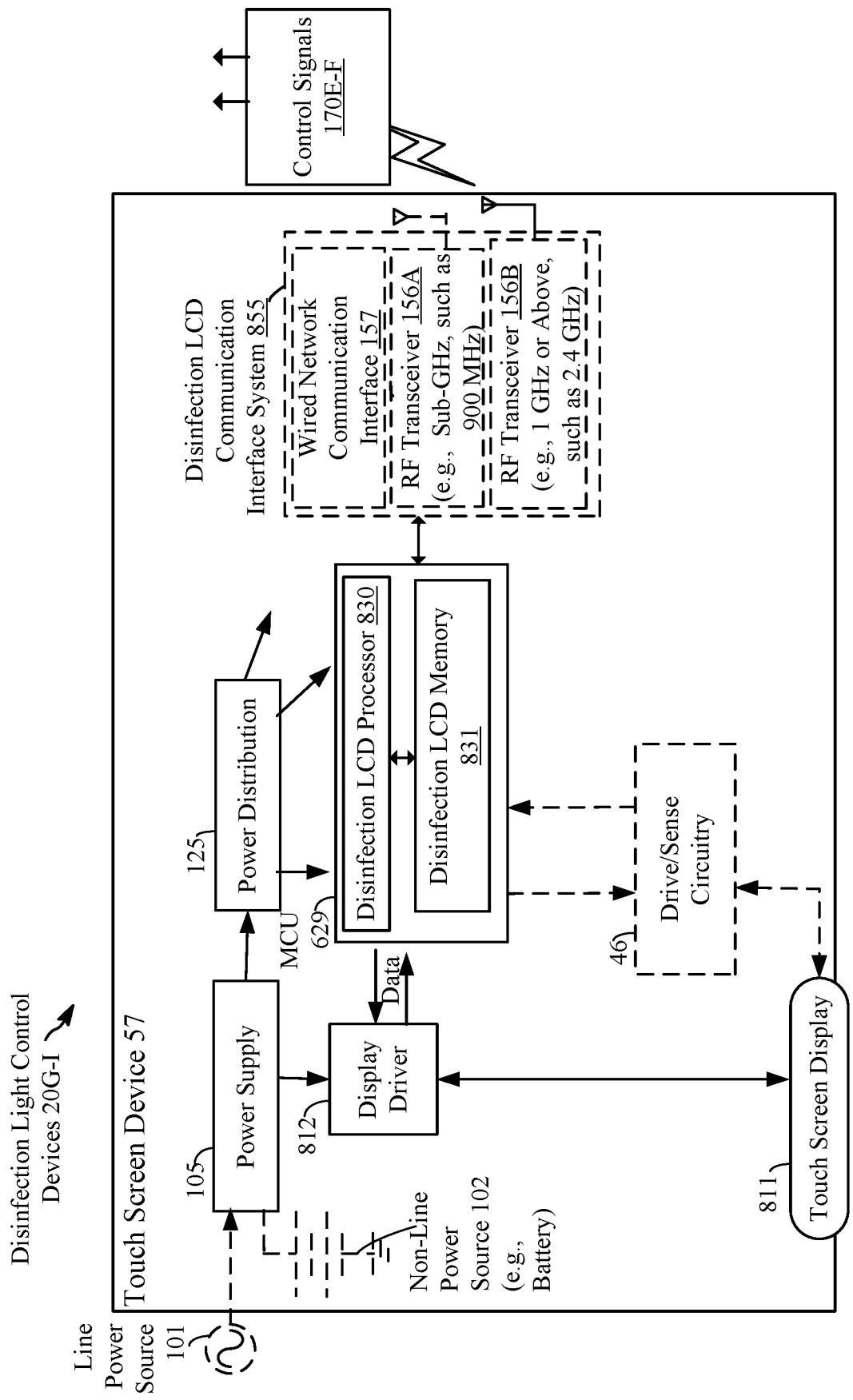
FIG. 8B is a block diagram of a disinfection light control devices that is a touch screen device.

Luminaire processor 130, sensor processor 630 of FIG. 6, pathogen sensor processor 730 of FIG. 7, and disinfection LCD processor 830 of FIGS. 8A-B serve to perform various operations, for example, in accordance with instructions or programming executable by processors 130, 630, 730, 830. For example, such operations may include operations related to communications with various antimicrobial system 1 elements, such as luminaires 10A-N and disinfection light control devices 20A-M during the disinfection light exposure and dosage control protocol procedure described herein. Although a processor 130, 630, 730, 830 may be configured by use of hardwired logic, typical processors are general processing circuits configured by execution of programming. Processors 130, 630, 730, 830 include elements structured and arranged to perform one or more processing functions, typically various data processing functions. Although discrete logic components could be used, the examples utilize components forming a programmable CPU. A processor 130, 630, 730, 830 for example includes one or more integrated circuit (IC) chips incorporating the electronic elements to perform the functions of the CPU. The processors 130, 630, 730, 830 for example, may be based on any known or available microprocessor architecture, such as a Reduced Instruction Set Computing (RISC) using an ARM architecture, as commonly used today in mobile devices and other portable electronic devices. Of course, other processor circuitry may be used to form the CPU or processor hardware in. Although the illustrated examples of the processors 130, 630, 730, 830 include only one microprocessor, for convenience, a multi-processor architecture can also be used. A digital signal processor (DSP) or field-programmable gate array (FPGA) could be suitable replacements for the processors 130, 630, 730, 830, but may consume more power with added complexity.

Luminaire memory 131, sensor memory 631 of FIG. 6, pathogen sensor memory 731 of FIG. 7, and disinfection LCD memory 831 of FIGS. 8A-B are for storing data and programming. In the example, the main memory system 131, 631, 731, 831 may include a flash memory (non-volatile or persistent storage) and/or a random access memory (RAM) (volatile storage). The RAM serves as short term storage for instructions and data being handled by the processors 130, 630, 730, 830 e.g., as a working data processing memory. The flash memory typically provides longer term storage.

Of course, other storage devices or configurations may be added to or substituted for those in the example. Such other storage devices may be implemented using any type of storage medium having computer or processor readable instructions or programming stored therein and may include, for example, any or all of the tangible memory of the computers, processors or the like, or associated modules.

FIG. 2 is a high-level functional block diagram of an example of an antimicrobial system 1 that includes thirteen luminaires 10A-N like that of FIG. 1 and twelve disinfection light control devices 20A-M. Antimicrobial system 1 implements the disinfection light exposure and dosage limit control protocol. As described herein, the disinfection exposure and dosage control protocol also includes communications in support of turning a disinfection light source 16 of luminaires 10-N on/off, adjusting intensity, sensor trip events, and other control signals 170A-N. As shown, the control signals 170E-N can be received from disinfection light control devices 20A-M via the disinfection light control network 7.

Antimicrobial system 1 may be designed for a physical space 2 (e.g., on-premises), which can be indoor or outdoor. As shown in the example, antimicrobial system 1 includes a variety of lighting network elements, including luminaires 10A-N and disinfection light control devices 20A-M. Luminaires 10A-N can be coupled via a disinfection light control network 7 (e.g., wired or wireless network) to various disinfection light control devices 20A-M to receive control signals 170E-N for the disinfection light via the disinfection light network 7 or alternatively include (e.g., integrate or incorporate) disinfection light control devices 20A-C to receive control signals 170A-C for the disinfection light 17.

Antimicrobial system 1 provides a variety of disinfection light controls of a disinfection light control group 8 over the disinfection light control network 7. For purposes of communication and control, each luminaire 10A-N and disinfection light control device 20A-M is treated as a single or a multi-addressable device that can be configured to operate as a respective member 6A-Y of the disinfection light control group 8 that communicates over the disinfection light control network 7.

When equipped with disinfection light control devices 20A-M and luminaires 10A-N, the disinfection light exposure and dosage limit control protocol implemented by the antimicrobial system can proceed as follows. Execution of the exposure and dosage control programming 132 by the luminaire processor 130 configures the luminaire 10 to perform the following functions. First, the luminaire 10 receives the control signal 170 from the disinfection light control device 20. Second, in response to receiving the control signal 170, the luminaire 10 controls, via the driver circuit 11, the disinfection light source 16 over the dose cycle 136 to emit the disinfection light 17 continuously or during the plurality of periods 137A-N for disinfecting the vicinity 180 to substantially obtain the target pathogen UV radiation level 139 and restrict the total UV radiation threshold exposure level 135 by the UV radiation threshold limit 133.

The control signal 170 can include: (i) a first sensing signal 170A from a detector 47 indicating that the human 185 is not present in the vicinity 180, (ii) a second sensing signal 170B from a pathogen sensor 48 indicating that the target pathogen 187 is present in the vicinity 180, (iii) an on/off signal 170C responsive to a wall switch 56 or a touch screen device 57, (iv) a time of day 170D for disinfection the vicinity 180, or (v) or a combination thereof.

Hence, control operations for the disinfection light 17 of the antimicrobial system 1 can involve networked collaboration between the luminaires 10A-N and the disinfection light control devices 20A-M that comprise the disinfection light control group 8. In the example, the disinfection light control group 8 includes a plurality of member devices 6A-Y (25 devices total), which are shown as the luminaires 10A-N and disinfection light control devices 20A-M. Luminaires 10A-N can receive the control signals 170E-N from disinfection light control devices 20A-M via the disinfection light control network 7. All or some of the components of the depicted disinfection light control devices 20A-M, such as occupancy, daylight, or audio sensors 45A-C and pathogen sensors 48A-C, etc. can be directly incorporated into the luminaires 10A-N, as shown in FIG. 1.

Disinfection light control devices 20A-C include occupancy, daylight, or audio sensors 45A-C to enable controls for occupancy and intensity adjustment of the disinfection 17. As shown, disinfection light control devices 20D-F are wall switches 56A-C; disinfection light control devices 20G-I are touch screen devices 57A-C; disinfection light control devices 20J-L are pathogen sensors 48A-C; and disinfection light control device 20M is a mobile device 25. Generally, the disinfection light control devices 20A-M execute a disinfection application 223, as shown for mobile device 25, for communication of disinfection light control and system information over the disinfection light control network 7, e.g., to transmit the control signals 170D-N to luminaires 10A-N.

As shown, each of the luminaires 10A-N include an on-board luminaire control circuit 12, such as a micro-control unit (MCU), that includes a luminaire memory 131 (volatile and non-volatile) and a central processing unit (CPU) 130. As shown, the control circuit 12 of the luminaires 10A-N is coupled to a driver circuit 11 that controls light source operation of a disinfection light source 16 and an optional general illumination light source 18. Occupancy, daylight, or audio sensors 45A-C have a micro-control unit (MCU) coupled to drive/sense circuitry 46 operable to control detectors 47 (e.g., occupancy, daylight, or audio sensors). Pathogen sensors 48A-C have an MCU that includes a sense circuit 50 operable to control a spectrometer 49.

Luminaires 10A-N and disinfection light control devices 20A-M can communicate control signal(s) 170E-N for the disinfection light 10 over a wireless disinfection light control network 7 (e.g., 900 MHz) and accordingly each include a first radio 156A in the sub-GHz range. A variety of control signals 170E-N for the disinfection light 17 are transmitted over wireless disinfection light control network 7, including, for example, to turn the disinfection light source 16 on/off and sensor trip events. In a first example, each luminaire 10A-N and disinfection light control device 20A-M is also equipped with a second above 1 GHz radio 156B (e.g., near range 2.4 GHz Bluetooth Low Energy (BLE)) that communicates over a separate commissioning network (not shown) for purposes of commissioning and maintenance of the antimicrobial system 1, however no control signals 170E-N for the disinfection light 17 pass over this commissioning network. In a second example, wireless disinfection light control network 7 and commissioning network are combined, such that both control signals 170E-N for disinfection light 17 and commissioning/maintenance information pass over the above 1 GHz range wireless communication band. In the second example, luminaires 10A-N and disinfection light control devices 20A-M are only equipped with the above 1 GHz radio 156B for communication of control signals 170E-N for disinfection light 17 and commissioning/maintenance information.

The antimicrobial system 1 can be provisioned with a mobile device 25 that includes a commissioning/maintenance application (not shown) for commissioning and maintenance functions of the antimicrobial system 1. For example, mobile device 25 enables mobile commissioning, configuration, and maintenance functions and can be a PDA or smartphone type of device with human interfacing mechanisms sufficient to perform clear and uncluttered user directed operations. Mobile device 25 runs mobile type applications on iOS7, Android KitKat, and windows 10 operating systems and commissioning/maintenance application to support commissioning.

Antimicrobial system 1 can leverage existing sensor and fixture control capabilities of Acuity Brands Lighting's commercially available nLight® wired product through firmware reuse. In general, Acuity Brands Lighting's nLight® wired product provides the lighting control applications. However, the illustrated antimicrobial system 1 includes a communications backbone and includes model—transport, network, media access control (MAC)/physical layer (PHY) functions. The sub-GHz communications of the wireless disinfection light control network 7 features are built on a near 802.15.4 MAC and PHY implantation with network and transport features architected for special purpose control and air time optimizations to limit chatter.

Antimicrobial system 1 further includes a gateway 220. The gateway 220 is a computing device that provides access between a wide area network (WAN) 255 and a local communication network, such as the disinfection light control network 7. The WAN 255 (e.g., Internet) can be a cellular network, optical fiber, cable network, or satellite network that can be connected to via Ethernet, for example. The gateway 220 may provide routing, access, and other services for the luminaires 10A-N and the disinfection light control devices 20A-M residing at the physical space 2, for example.

Antimicrobial system 1 further includes a cloud computing device 266, and the cloud computing device 266 resides off-premises 265 (e.g., cloud) meaning the cloud computing device 266 is a remote computing device or server hosted on the Internet to store, manage, and process data, rather than the local gateway 220. The gateway 200, cloud computing device 266, or mobile device 25 (via disinfection app 223) can also be used to monitor and control (e.g., switch on/off) the disinfection light 17 of the luminaires 10A-N and other components of the antimicrobial system 1, such as disinfection light control devices 20A-M. Gateway 220, cloud computing device 266, and mobile device 25 can receive and process data from the luminaires 10A-N and the disinfection light control devices 20A-M. For example, the gateway 220, cloud computing device, and mobile device 25 can adjust the total UV radiation threshold limit 133, target pathogen radiation level 139, desired amount 140 (e.g., desired log reduction), super dose level 142, rated lifetime limit 145, and other parameters of the dose cycle 136.

Antimicrobial system 1 can be deployed in standalone or integrated environments. Antimicrobial system 1 can be an integrated deployment, or a deployment of standalone groups with no gateway 220. One or more disinfection light control groups 8A-N of antimicrobial system 1 may operate independently of one another with no backhaul connections to other networks. Antimicrobial system 1 may comprise a mix and match of various indoor systems, wired lighting systems (nLight® wired), emergency, and outdoor (dark to light) products that are networked together to form a collaborative and unified lighting solution. Additional control devices and lighting fixtures, gateway(s) 220 for backhaul connection, time sync control, data collection and management capabilities, and interoperation with the Acuity Brands Lighting's commercially available SensorView™ product may also be provided.

The instructions, programming, or application(s) implementing the disinfection light exposure and dosage limit control protocol described herein may be software or firmware used to implement any other device functions associated with luminaires 10A-N, disinfection light control devices 20A-M, network controller (e.g., gateway 220), and cloud computing device 266. Program aspects of the technology may be thought of as "products" or "articles of manufacture" typically in the form of executable code or process instructions and/or associated data that is stored on or embodied in a type of machine or processor readable medium (e.g., transitory or non-transitory), such as memory 131, 631, 731, 831; a memory of gateway 220 or cloud computing device 266; and/or another computer used to download or otherwise install such programming into the with luminaires 10A-N, disinfection light control devices 20A-M, network controller (e.g., gateway 220), cloud computing device 266, or a transportable storage device or a communications medium for carrying program for installation in the luminaires 10A-N, disinfection light control devices 20A-M, network controller (e.g., gateway 220), and/or cloud computing device 266.

Figure 3:
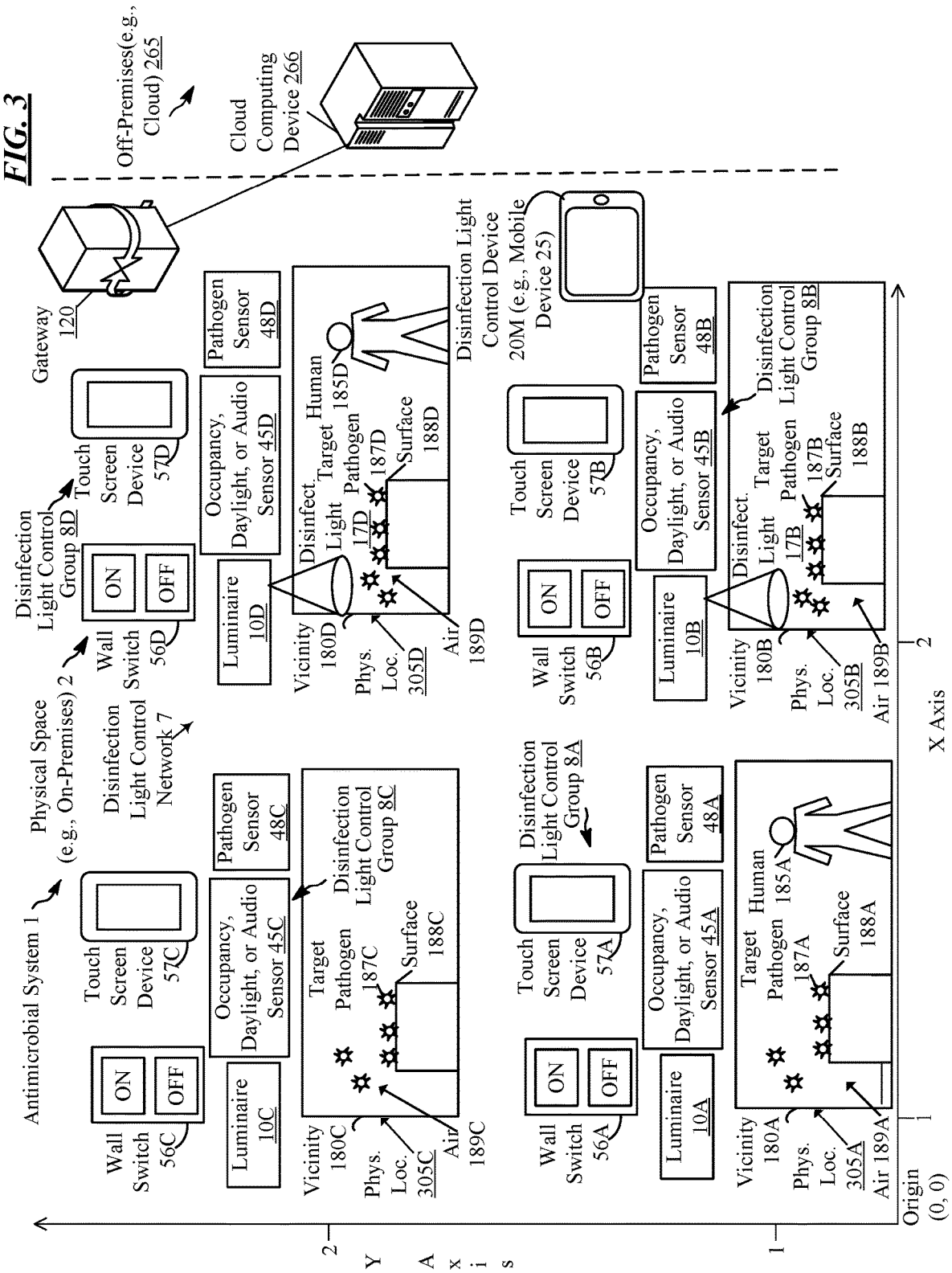
FIG. 3 illustrates tying the control of a disinfection light source of the luminaire to the position of an occupant (e.g., human) in the physical space.

FIG. 3 depicts tying the control of a disinfection light source 17 of the luminaire 10 to the position of an occupant (e.g., human 185) in the physical space 2. In the example of FIG. 3, the disinfection light 17 is emitted as the human 185 moves away from a respective vicinity 180A-D of a respective luminaire 10A-D.

A plurality of disinfection light control groups 8A-D can exist in the disinfection light control network 7 that is comprised of luminaires 10A-N and disinfection light control devices 20A-N. In the example of FIG. 2, the physical space 2 on-premises (e.g., interior to a building or exterior) is comprised of four disinfection light control groups 8A-D in a respective vicinity 180A-D each operating independently of one another. The vicinities 180A-D are at different respective physical locations 305A-D throughout the physical space 2. Specifically, vicinity 180A is at a first physical location 305A with location coordinates (1,1); vicinity 180B is at physical location 305B with location coordinates (2,1); vicinity 180C is at physical location 305C with location coordinates (1,2); and vicinity 180D is at physical location 305D with location coordinates (2,2). Each disinfection light control group 8A-D operates in a respective vicinity 180A-D of the physical space 2 to disinfect a respective surface(s) 188A-D and respective air 189A-D of a respective target pathogen 187A-D.

Each disinfection light control group 8A-D can have a group monitor, which can be a respective luminaire 10A-D. For example, as shown in FIG. 3, disinfection light control group 8A includes a respective vicinity 180A at physical location 305A in which luminaire 10A along with any combination of occupancy, daylight, or audio sensor 45A; switch 56A; touch screen device 57A; and pathogen sensor 48A are located. Similarly, disinfection light control group 8B includes a respective vicinity 180B at physical location 305B in which luminaire 110B along with any combination of occupancy, daylight, or audio sensor 45B; wall switch 56B; touch screen device 57B; pathogen sensor 48B; and mobile device 25 are located. Disinfection light control group 8C includes a respective vicinity 180C at physical location 305C in which luminaire 110C along with any combination of occupancy, daylight, or audio sensor 45C; wall switch 56C; touch screen device 57C; pathogen sensor 48C are located. Disinfection light control group 8D includes a respective vicinity 180D at physical location 305D in which luminaire 110D along with any combination of occupancy, daylight, or audio sensor 45D; wall switch 56D; touch screen device 57D; pathogen sensor 48D are located.

As shown, a human 185A is in vicinity 180A and another human 185D is in vicinity 180D. Hence, disinfection light control groups 8A-D are controlled, such that only disinfection light source 16B of luminaire 10B emits disinfection light 17B and disinfection light source 16C of luminaire 10C emits disinfection light 17C because only vicinities 180B and 180C are unoccupied by humans.

Controlling the luminaires 10A-N by occupant position allows a physical space 2, such as a large room (e.g., store), to have disinfection light 17 on in part of the room and not significantly irradiating a different part of the physical space 2. A human 185 in the non-irradiated part of the large room will not be irradiated and this allows the physical locations 305B, 305C of the large room to be disinfected at rates well above the UV radiation threshold limit 133, e.g., at a super dose level 142, but in an accelerated super dose time period.

Accordingly, as shown in FIG. 3, the antimicrobial system 1 includes a plurality of disinfection light control devices 20A-D (e.g., occupancy, daylight, or audio sensors 45A-D). A respective disinfection light control device 20A-D generates a respective control signal 170A-D to control emission of a respective disinfection light source 16A-N in a respective vicinity 180A-D of the physical space 2. Antimicrobial system 1 includes a plurality of luminaires 10A-D. A respective luminaire 10A-D is coupled to the respective disinfection light control device 20A-D and includes a respective disinfection light source 16A-D to emit the respective disinfection light 17A-D for disinfection the respective vicinity 180A-D of the physical space 2, and a respective driver circuit 11A-D. Execution of the exposure and dosage control programming 132 by a respective luminaire processor 130A-D configures the respective luminaire 10A-D to perform the following functions. The respective luminaire 10A-D receives the respective control signal 170A-D from the respective disinfection light control device 20A-D. In response to receiving the respective control signal 170A-D, the respective luminaire 10A-D controls, via the respective driver circuit 11A-D, the respective disinfection light source 16A-D over a respective dose cycle 136A-D to emit the respective disinfection light 17A-D for disinfecting the respective vicinity 180A-D to substantially obtain a respective target pathogen UV radiation level 139A-D and restrict a respective total UV radiation threshold exposure level 135A-D by a respective UV radiation threshold limit 133A-D.

FIGS. 4A-D depict a variety of disinfection status indicators 400A-D to convey a visible cue to a human 185 of a disinfection state 405A-D of the vicinity 180. The disinfection status indicators 400A-D can be visibly presented to the human 185 on a display coupled (e.g., mounted) to the luminaires 10A-N, disinfection light control devices 20A-M (e.g., wall switches 46A-C, touch screen devices 47A-C, mobile device 25, etc.), gateway 220, or cloud computing device 266 of antimicrobial system 1. For example, disinfection status indicator 400D that the vicinity 180 (e.g., room) has obtained the required dose can be displayed on the room controller or on a different device, such as a smart phone, tablet, or a computer. The disinfection status indicator 400 can be a display that is controlled by the antimicrobial system 1 to indicate the state of the vicinity (e.g., room), such as a sign on the wall or door. This can be accomplished with calculations and timing using radiation calculation software or with separate UV disinfection light 17 measurement equipment either in the vicinity 180 or on the luminaire 10 emitting the disinfection light 17.

Figure 4A:
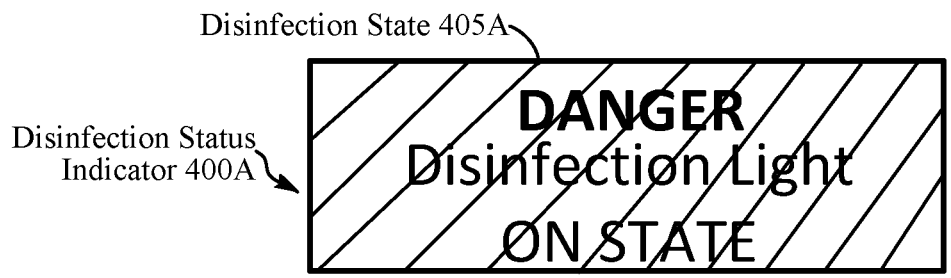
FIGS. 4A-D depict a variety of disinfection status indicators to convey a visible cue to a human of a disinfection state of a vicinity.
Figure 4B:
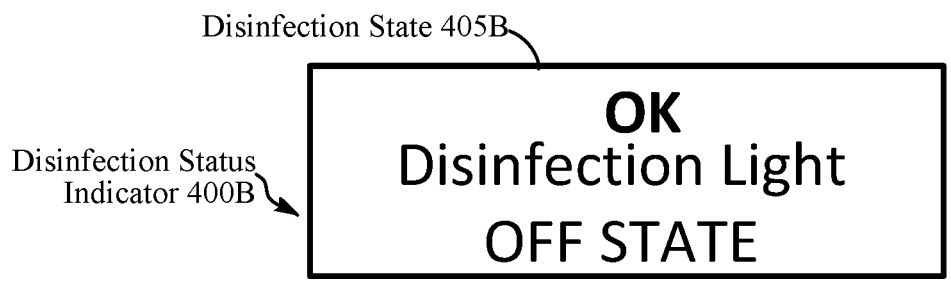
Figure 4C:
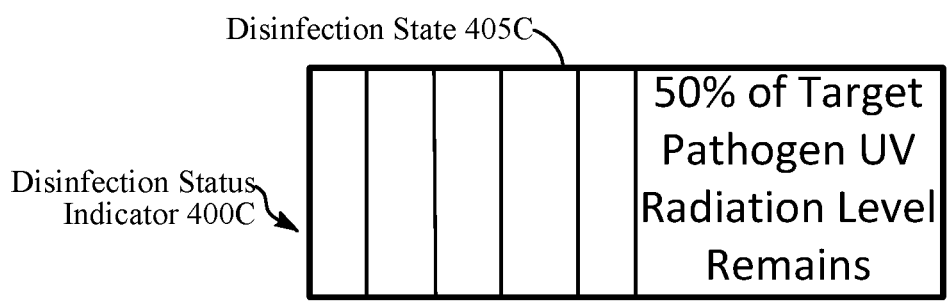
Figure 4D:
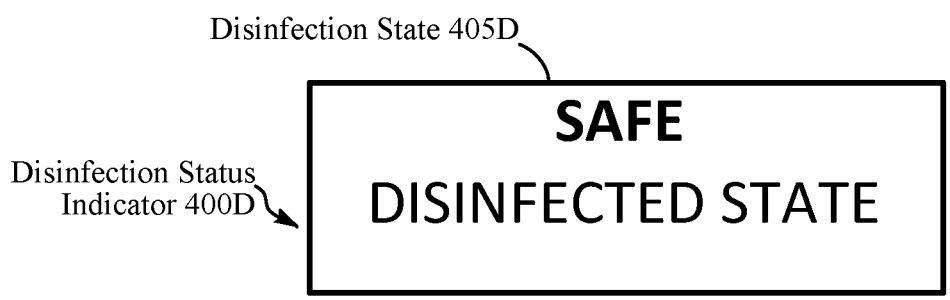

As shown in FIG. 4A, the disinfection status indicator 400A indicates the disinfection state 400A is that the disinfection light source 16 is in an on state of actively emitting the disinfection light 17 for disinfecting the vicinity 180 (e.g., room). As shown in FIG. 4B, the disinfection status indicator 400B indicates the disinfection state 405B is that the disinfection light source 16 is in an off state of no longer actively emitting the disinfection light 17 for disinfecting the vicinity 180. As shown in FIG. 4C, the disinfection status indicator 400C indicates the disinfection state 405C is at a percentage or a portion (e.g. of a 24 hour dose) of the target pathogen UV radiation level 139 over the predetermined dose period 134. As shown in FIG. 4D, the disinfection status indicator 400D indicates the disinfection state 405D is in a "disinfected state," such that the vicinity 180 is disinfected of the target pathogen 187 by reducing the target pathogen 187 by a desired amount 140, e.g., a desired log reduction. In the example of FIG. 4, the "disinfected state" is achieved after the target pathogen UV radiation level 139 is obtained over the dose cycle 136, e.g., the vicinity 180 has received a full dose of disinfection light 17.

Antimicrobial system 1 can include a variety of other visible examples of the disinfection status indicator 400, for example, an indicator lamp coupled (e.g., mounted) to the luminaire 10 or located inside or outside the vicinity 180 of the physical space 2 (e.g., room). Other visible examples of the disinfection status indicator 400 include a lumiphore coupled to the luminaire 10 or located inside or outside the vicinity 180 of the physical space 2. The lumiphore includes one or more materials, such as a phosphor, a nano-phosphor, a phosphorescent, and/or a metamaterial, etc. that converts light from one wavelength to another (e.g., UV disinfection light 17 to visible light) and the light wavelength conversion is visible to the human 185 as glow (e.g., fluorescence). Such an example of the a lumiphore type of disinfection status indicator 400 to visibly indicate to the human 185 the presence and intensity of UV disinfection light 17 are disclosed in U.S. patent application Ser. No. 16/848,226, filed Apr. 14, 2020, titled "Indication of Ultraviolet (UV) Light Intensity Using a Lumiphore," the entirety of which is incorporated by reference herein. Audible examples of the disinfection status indicator 400 include a speaker coupled to the luminaire 10 or located inside or outside the vicinity 180 of the physical space 2. The disinfection status indicator 400 can also be a tactile indication on a door that the human 185 uses to enter the vicinity 180.

Figure 5:
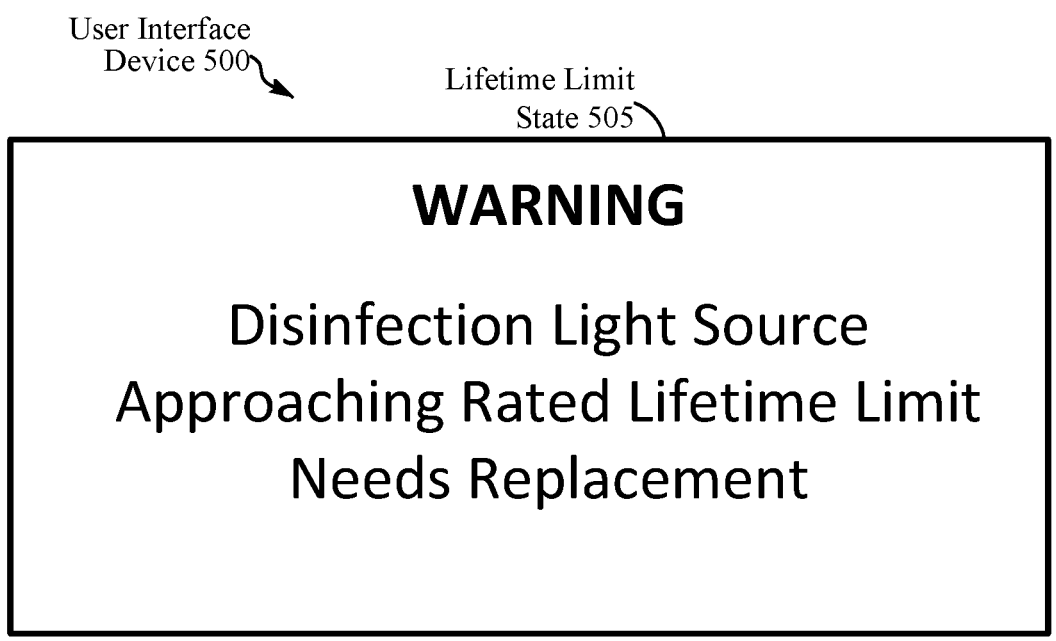
FIG. 5 depicts a user interface device that displays a lifetime limit state of the disinfection light source of the luminaire.

FIG. 5 depicts a user interface device 500 that displays a lifetime limit state 505 of the disinfection light source 16 of the luminaire 10. Like the disinfection status indicators 400A-D, the lifetime limit state 505 is visibly presented to the human 185 on a display of a user interface device that is coupled to the luminaire 10. For example, any of the disinfection light control devices 20A-M (e.g., wall switches 46A-C, touch screen devices 47A-C, mobile device 25), gateway 220, or cloud computing device 266 of the antimicrobial system 1 can include the user interface device 500. For example, the lifetime limit state 505 of the disinfection light source 16 can be displayed on the user interface device 500, such as the room controller or on a different device, such as a smart phone, tablet, or a computer. The user interface device 500 can be a display controlled by the antimicrobial system 1 to display the state of the disinfection light source 16, such as a sign on the wall or door.

In the example of FIG. 5, the disinfection light source device 20G (e.g., touch screen device 57A) includes the user interface device 500 that displays the lifetime limit state 505 indicating that the disinfection light source 16 is approaching the rated lifetime limit 145 and needs replacement. To enable the display of the lifetime limit state 505 to the human 185 on the user interface device 500, the luminaire memory 131 includes a rated lifetime limit 145 for the disinfection light source 16 and a total disinfection light source on time 143 that specifies a cumulative on time that the disinfection light 17 is emitted from the disinfection light source 16 over a lifetime. Execution of the exposure and dosage control programming 132 by the luminaire processor 130 configures the luminaire 10 to perform the following functions. First, the luminaire 10 determines that the total disinfection light source on time 143 is approaching the rated lifetime limit 145 of the disinfection light source 16. Second, in response to determining that the total disinfection light source on time 143 is approaching the rated lifetime limit 145 of the disinfection light source 16, the luminaire 10 warns, via the user interface device 500, that the disinfection light source 16 needs replacement. The user interface device 500 can communicate over the disinfection light control network 7 with the gateway 220, cloud computing device 266, and other devices of the antimicrobial system 1, such as a robot (not shown) to enable replacement of the disinfection light source 16.

FIG. 6 is a block diagram of a disinfection light control device 20A-C that is an occupancy, audio, or daylight sensor 45. The occupancy, audio, or daylight sensor 45 can be a standalone device in the antimicrobial system 1 as shown in FIG. 2 or included (e.g., integrated) in the luminaire 10 as shown in FIG. 1. Occupancy, audio, or daylight sensor 45 includes a micro-control unit (MCU) 629, drive/sense circuitry 46, detector(s) 47 (e.g., occupancy, daylight, or audio), and an optional sensor communication interface system 655. As shown, MCU 629 includes sensor processor 630 and sensor memory 631 to implement the disinfection light exposure and dosage limit control protocol described herein.

The circuitry, hardware, and software of the occupancy, audio, or daylight sensor 45 is similar to the luminaire 10 of FIG. 1, including the line power source 101, non-line power source 102, power supply 105, power distribution 125, and the sensor communication interface system 655. If the occupancy, audio, or daylight sensor 45 is a standalone device, then the occupancy, audio, or daylight sensor 45 can include a sensor communication interface system 655 like the luminaire communication interface system 155 of FIG. 1. If the occupancy, audio, or daylight sensor 45 is integrated into the luminaire 10 like that shown in FIG. 1, then the occupancy, audio, or daylight sensor 45 does not include the sensor communication interface system 655.

FIG. 7 is a block diagram of a disinfection light control device 20J-L that is a pathogen sensor 48. Pathogen sensor 48 can be a standalone device in the antimicrobial system 1 as shown in FIG. 2 or included (e.g., integrated) in the luminaire 10 as shown in FIG. 1. Pathogen sensor 48 includes a spectrometer 49, a sense circuit 50, and an optional sensor communication interface system 655.

The circuitry, hardware, and software of the pathogen sensor 48 is similar to the luminaire 10 of FIG. 1, including the line power source 101, non-line power source 102, power supply 105, power distribution 125, and the sensor communication interface system 655. If the pathogen sensor 48 is a standalone device, then the pathogen sensor can include a sensor communication interface system 655 like the luminaire communication interface system 155 of FIG. 1. If the pathogen sensor 48 is integrated into the luminaire 10 like that shown in FIG. 1, then the pathogen sensor 48 does not include the sensor communication interface system 655.

Sense circuit 50 of the pathogen sensor 48 can be an MCU 629 that includes a pathogen sensor processor 730 and a pathogen sensor memory 731. Pathogen sensor memory 731 can include spectral reference data 752, such as a spectral power distribution, known to be associated with various types of target pathogens 187A-N. Pathogen sensor processor 730 compares the spectral reference data 752 stored in the pathogen sensor memory 731 with a spectral power measurement 753 received from the spectrometer 49. The comparison compares the spectral power measurement 753 to the spectral reference data 752 to determine the presence of any type of target pathogen 187. The pathogen sensor 48 transmits the detection of the target pathogen 187 as the second control (e.g., sensing) signal 170B to the luminaire 10.

Pathogen sensor 48 may also determine a specific target pathogen identifier 754 of the target pathogen 187. To determine a specific target pathogen identifier 754, if there is a match to a specific spectral reference data 752A of a plurality of spectral reference data 752A-N, where each respective spectral reference data 752A-N is known to correspond to a specific respective target pathogen 187A-N, then the pathogen sensor processor 730 determines a respective target pathogen identifier 754A-N. The pathogen sensor 48 transmits the determined target pathogen identifier 754 as the second control (e.g., sensing) signal 170B to the luminaire 10. The luminaire processor 130 can adjust the target pathogen UV radiation level 139, the desired amount 140 (e.g., desired log reduction), or other parameters of the dose cycle 136 based on the target pathogen identifier 754. For example, assume a first target pathogen 187A associated with a first determined target pathogen identifier 754A has a first target pathogen UV radiation level 139A of approximately 10-15 mJ/cm$^2$ and a second pathogen 187B associated with a second determined target pathogen identifier 754B has a second target pathogen UV radiation level 139B of approximately 20-25 mJ/cm$^2$. In this example, the adjusted target pathogen UV radiation level 139 is set to a maximum of the first target pathogen UV radiation level 139A of the second target pathogen UV radiation level 139B, that is, the first target pathogen UV radiation level 139A of 20-25 mJ/cm$^2$ and the dose cycle 136 can be adjusted.

Light irradiation calculation programming (not shown) can estimate dosing levels for the disinfection light 17 in one or more vicinities 180A-D of the physical space 2 to determine (e.g., precalculate) the target pathogen UV radiation levels 139A-B for the target pathogen identifiers 754A-B stored in the luminaire memory 131 of the luminaire 10. The light irradiation calculation program calculates lighting levels (e.g., intensity and/or uniformity) of the disinfection light 17 in vicinities 180A-D of the physical space 2 (e.g., including surface(s) 188 and air 189). Based on the calculated lighting levels of the disinfection light 17, the exposure and dosage control programming 132 adjusts the target pathogen UV radiation levels 139A-B for the target pathogen identifiers 754A-B stored in the memory 131. The light irradiation calculation program can be implemented in various devices of the antimicrobial system 1, including the luminaire 10, mobile device 25, gateway 220, and/or cloud computing device 266.

Alternatively or additionally this logic of the sense circuit 50 of the pathogen sensor 48 can be implemented within the luminaire 10. Hence, luminaire memory 131 can include the spectral reference data 752 and the luminaire processor 130 compares the spectral reference data 752 stored in the memory 131 with the spectral power measurements 753 received as the second control (e.g., sensing) signal 170B from the sense circuit 50. If there is a match, the luminaire processor 130 determines target pathogen identifier 754. Based on the target pathogen identifier 754, the luminaire processor 130 can adjust the target pathogen UV radiation level 139, the desired amount 140 (e.g., desired log reduction), or other parameters of the dose cycle 136.

FIG. 8A is a block diagram of disinfection light control devices (LCDs) 20D-F that are a wall switch 56. FIG. 8B is a block diagram of disinfection LCDs 20G-I that are a touch screen device 57. The circuitry, hardware, and software of the wall switch 56 and the touch screen device 57 shown are similar to the luminaire 10 of FIG. 1, including the disinfection LCD communication interface system 855. As shown, both the wall switch 56 and the touch screen device include an MCU 629 that includes a disinfection LCD memory 830 and disinfection light control device processor 831 to implement the disinfection light exposure and dosage limit control protocol described herein.

As shown in FIG. 8A, the drive/sense circuitry 46 of the wall switch 56 responds to switches 861. Switches 861 can be an on/off switch, dimmer switch, etc. to control the disinfection light source 17 of the luminaire 10 based on Acuity Brands Lighting's commercially available xPoint® Wireless ES7 product. In some examples, wall switch 56 includes a single shared button switch 861 for on/off, dimming, or other functions and a pilot light source indicator (not shown) of wall switch 56. A button station can include various button settings that can have the settings for the disinfection light 17 emitted from the luminaire 10 adjusted, for example, four buttons can be arranged with two longitudinal buttons (north-south) and two lateral buttons (east-west).

In FIG. 8B, the touch screen device 57 enables setting adjustments for the disinfection light source 17 emitted from the luminaire 10 to be inputted via a user interface application (not shown) through manipulation or gestures on a touch screen display 811. For output purposes, the touch screen display 811 includes a display screen, such as a liquid crystal display (LCD) or light emitting diode (LED) screen or the like. For input purposes, the touch screen display 811 includes a plurality of touch sensors.

A keypad may be implemented in hardware as a physical keyboard of touch screen device 57, and keys may correspond to hardware keys of such a keyboard. Alternatively, some or all of the keys (and keyboard) of touchscreen device 57 may be implemented as "soft keys" of a virtual keyboard graphically represented in an appropriate arrangement via touch screen display 811. The soft keys presented on the touch screen display 811 may allow the user of touchscreen device 57 to invoke the same user interface functions as with the physical hardware keys.

Drive/sense circuitry 46 is coupled to touch sensors of touch screen display 811 for detecting the occurrence and relative location/position of each touch with respect to a content display area of touch screen display 811. In this example, drive/sense circuitry 46 is configured to provide disinfection LCD processor 830 with touch-position information based on user input received via touch sensors. In some implementations, disinfection LCD processor 830 is configured to correlate the touch position information to specific content being displayed within the content display area on touch screen display 811. The touch-position information captured by the drive/sense circuitry 46 and provided to disinfection LCD processor 830 may include, but is not limited to, coordinates identifying the location of each detected touch with respect to the display area of touch screen display 811 and a timestamp corresponding to each detected touch position.

In general, touch screen display 811 and its touch sensors (and one or more keys, if included) are used to provide a textual and graphical user interface for the touch screen device 57. In an example, touch screen display 811 provides viewable content to the user at disinfection light control devices 20G-I. Touch screen device 57 also enables the user to interact directly with the viewable content provided in the content display area, typically by touching the surface of the screen with a finger or an implement such as a stylus.

Any of the steps or functionality, e.g., of the disinfection light control techniques, such as disinfection light exposure and dosage limit control protocol, described herein for luminaires 10A-N, disinfection light control devices 20A-M, gateway 220, cloud computing device 266, can be embodied in programming or one or more applications as described previously. This includes, for example, exposure and dosage control programming 132, disinfection application 223, and pathogen sensor programming 751. According to some embodiments, "function," "functions," "application," "applications," "instruction," "instructions," or "programming" are program(s) that execute functions defined in the programs. Various programming languages can be employed to create one or more of the applications, structured in a variety of manners, such as object-oriented programming languages (e.g., Objective-C, Java, or C++), procedural programming languages (e.g., C or assembly language), or firmware. In a specific example, a third party application (e.g., an application developed using the ANDROID™ or IOS™ software development kit (SDK) by an entity other than the vendor of the particular platform) may be mobile software running on a mobile operating system such as IOS™, ANDROID™ WINDOWS® Phone, or another mobile operating systems. In this example, the third party application can invoke API calls provided by the operating system to facilitate functionality described herein.

Hence, a machine-readable medium may take many forms of tangible storage medium. Non-volatile storage media include, for example, optical or magnetic disks, such as any of the storage devices in any computer(s) or the like, such as may be used to implement the client device, media gateway, transcoder, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims. It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as ±10% from the stated amount. As used herein, the terms "substantially" or "approximately" mean the parameter value varies up to ±10% from the stated amount.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus the following claims are hereby incorporated into the Detailed Description, with each claim standing on its own as a separately claimed subject matter.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

The invention claimed is:

1. An antimicrobial system, comprising:
   a disinfection light control device to generate a control signal to control emission of a disinfection light in an ultraviolet (UV) band for disinfecting a vicinity of a space of a target pathogen;
   a luminaire including or coupled to the disinfection light control device, the luminaire comprising:
     a disinfection light source to emit the disinfection light in the UV band for disinfecting the vicinity of the space of the target pathogen that is exposed to the disinfection light, the UV band being between 200 nanometers (nm) to 230 nm;
     a driver circuit coupled to the disinfection light source to control light source operation of the disinfection light source;
     a luminaire control circuit including:
       a luminaire processor coupled to the driver circuit and configured to control the disinfection light source via the driver circuit;
       a luminaire memory accessible by the luminaire processor and including:
         a UV radiation threshold limit for safe exposure of a human to the UV band over a predetermined dose period,
         a total UV radiation threshold exposure level over a dose cycle of the vicinity, the dose cycle corresponding to the predetermined dose period or being a fraction or multiple thereof, and
         a target pathogen UV radiation level that is sufficient to reduce the target pathogen by a desired amount in the vicinity over the predetermined dose period; and
       exposure and dosage control programming in the luminaire memory, wherein execution of the exposure and dosage control programming by the luminaire processor configures the luminaire to perform functions, including functions to:
         receive the control signal from the disinfection light control device; and
         in response to receiving the control signal, control, via the driver circuit, the disinfection light source over the dose cycle to emit the disinfection light continuously or during a plurality of periods for disinfecting the vicinity to substantially obtain the target pathogen UV radiation level and restrict the total UV radiation threshold exposure level by the UV radiation threshold limit.

2. The antimicrobial system of claim 1, wherein:
   the function to control, via the driver circuit, the disinfection light source over the dose cycle further includes functions to:
     (a) emit the disinfection light for disinfecting the vicinity,
     (b) track an elapsed time of the dose cycle, (c) adjust the total UV radiation threshold exposure level based on the emission of the disinfection light continuously or during the plurality of periods, (d) determine whether the total UV radiation threshold exposure level falls below or exceeds the UV radiation threshold limit, and (e) determine whether the total UV radiation threshold exposure level falls below or exceeds the target pathogen UV radiation level.

3. The antimicrobial system of claim 2, wherein:
the function to control, via the driver circuit, the disinfection light source over the dose cycle further includes functions to:

(f) in response to determining that the total UV radiation threshold exposure level falls below the UV radiation threshold limit and falls below the target pathogen UV radiation level, repeat functions (a) to (e).

4. The antimicrobial system of claim 2, wherein:
the function to control, via the driver circuit, the disinfection light source over the dose cycle includes functions to:

(g) in response to determining that the total UV radiation threshold exposure level exceeds the UV radiation threshold limit or the target pathogen UV radiation level, end the dose cycle by disabling emission of the disinfection light for disinfecting the vicinity based on the elapsed time of the dose cycle and the predetermined dose period.

5. The antimicrobial system of claim 1, further comprising:
a disinfection status indicator to display a disinfection state of the vicinity, the disinfection state being:
(i) the disinfection light source is in an on state of actively emitting the disinfection light for disinfecting the vicinity,
(ii) the disinfection light source is at a percentage or a portion of the target pathogen UV radiation level over the predetermined dose period, or
(iii) the vicinity is in a disinfected state such that the target pathogen in the vicinity is reduced by the desired amount after the target pathogen UV radiation level is obtained over the dose cycle.

6. The antimicrobial system of claim 1, wherein:
the disinfection light control device includes a detector;
the control signal includes a first sensing signal that indicates a human is present in the vicinity; and
an elapsed time of the dose cycle tracks only when the human is present in the vicinity.

7. The antimicrobial system of claim 6, wherein:
the function to restrict the total UV radiation threshold exposure level by the UV radiation threshold limit includes to:
track the elapsed time of the dose cycle as a sum of a plurality of time durations that the human is present in the vicinity while the disinfection light is emitted from the disinfection light source;
determine the total UV radiation threshold exposure level across the plurality of time durations;
determine that the total UV radiation threshold exposure level is approaching the UV radiation threshold limit; and
in response to determining that the total UV radiation threshold exposure level is approaching the total UV radiation threshold limit, disable emission of the disinfection light from the disinfection light source while the human is present in the vicinity.

8. The antimicrobial system of claim 1, wherein:
the function to control, via the driver circuit, the disinfection light source over the dose cycle to emit the disinfection light includes to:
in response to receiving control signal, increase the emission of the disinfection light for disinfection the vicinity to a super dose level to accelerate deactivation of the target pathogen such that the UV radiation threshold limit is exceeded over the predetermined dose period.

9. The antimicrobial system of claim 8, wherein:
the luminaire memory includes a total disinfection light source on time that specifies a cumulative on time that the disinfection light is emitted from the disinfection light source over a lifetime;
the function to control, via the driver circuit, the disinfection light source over the dose cycle to emit the disinfection light includes to: based on the total disinfection light source on time: adjust a super dose time period of the super dose level to compensate for depreciation of the disinfection light source; and
the super dose time period of the super dose level is different earlier in the lifetime of the disinfection light source compared to later in the lifetime of the disinfection light source.

10. The antimicrobial system of claim 8, wherein:
the control signal includes:
(i) a first sensing signal from a detector indicating that the human is not present in the vicinity,
(ii) a second sensing signal from a pathogen sensor indicating that the target pathogen is present in the vicinity,
(iii) an on/off signal responsive to a wall switch or a touch screen device, or
(iv) a time of day for disinfection the vicinity,
(v) or a combination thereof.

11. The antimicrobial system of claim 10, wherein:
the disinfection light control device includes the pathogen sensor; and
the control signal includes the second sensing signal from the pathogen sensor.

12. The antimicrobial system of claim 1, wherein:
the luminaire memory includes a total disinfection light source on time that specifies a cumulative on time that the disinfection light is emitted from the disinfection light source over a lifetime; and
execution of the exposure and dosage control programming by the luminaire processor configures the luminaire to perform functions, including functions to:
monitor each time duration of past periods of the dose cycle that the disinfection light source is on;
update the total disinfection light source on time based on the monitored time durations; and
adjust future periods of the dose cycle based on the total disinfection light source on time.

13. The antimicrobial system of claim 1, wherein:
the disinfection light control device includes a user interface device;
the luminaire memory includes a rated lifetime limit for the disinfection light source and a total disinfection light source on time that specifies a cumulative on time that the disinfection light is emitted from the disinfection light source over a lifetime; and
execution of the exposure and dosage control programming by the luminaire processor configures the luminaire to perform functions, including functions to:

determine that the total disinfection light source on time is approaching the rated lifetime limit of the disinfection light source; and in response to determining that the total disinfection light source on time is approaching the rated lifetime limit of the disinfection light source, warn, via the user interface device, that the disinfection light source needs replacement.

14. The antimicrobial system of claim 1, further comprising:

a plurality of disinfection light control devices, wherein a respective disinfection light control device generates a respective control signal to control emission of a respective disinfection light source in a respective vicinity of the space;

a plurality of luminaires, wherein a respective luminaire is coupled to the respective disinfection light control device and includes a respective disinfection light source to emit the respective disinfection light for disinfection the respective vicinity of the space, and a respective driver circuit; and execution of the exposure and dosage control programming by a respective luminaire processor configures the respective luminaire to perform functions, including functions to:

receive the respective control signal from the respective disinfection light control device; and in response to receiving the respective control signal, control, via the respective driver circuit, the respective disinfection light source over a respective dose cycle to emit the respective disinfection light for disinfecting the respective vicinity to substantially obtain a respective target pathogen UV radiation level and restrict a respective total UV radiation threshold exposure level by a respective UV radiation threshold limit.

15. The antimicrobial system of claim 1, wherein:
the disinfection light control device includes a pathogen sensor; and
the control signal from the pathogen sensor includes a sensing signal that indicates the target pathogen is present in the vicinity.

16. The antimicrobial system of claim 15, wherein:
the pathogen sensor includes a spectrometer and a sense circuit to generate the sensing signal;
the sense circuit includes:
a pathogen sensor processor configured to control the spectrometer,
a pathogen sensor memory accessible to the pathogen sensor processor and storing spectral reference data of the target pathogen, and
pathogen sensor programming in the pathogen sensor memory; and
execution of the pathogen sensor programming by the pathogen sensor processor configures the pathogen sensor to perform functions, including functions to:
generate, via the spectrometer, a spectral power measurement for the vicinity by detecting, via the spectrometer, light passed, reflected, or shifted and regenerated by the target pathogen, and
compare, via the sense circuit, the spectral power measurement with the spectral reference data to generate the sensing signal indicating whether the target pathogen is present in the vicinity.

17. The antimicrobial system of claim 16, wherein:
the spectrometer is a Raman spectrometer.

* * * * *